(12) United States Patent
Endo et al.

(10) Patent No.: US 7,981,617 B2
(45) Date of Patent: Jul. 19, 2011

(54) TRANSCRIPTION TEMPLATE FOR CELL-FREE PROTEIN SYNTHESIS AND METHOD USING THE SAME

(75) Inventors: Yaeta Endo, Matsuyama (JP); Tatsuya Sawasaki, Matsuyama (JP); Tomio Ogasawara, Iyo (JP)

(73) Assignee: CellFree Sciences Co., Ltd., Kanagawa (JP)

( * ) Notice: Subject to any disclaimer, the term of this patent is extended or adjusted under 35 U.S.C. 154(b) by 1613 days.

(21) Appl. No.: 10/363,372

(22) PCT Filed: Aug. 28, 2001

(86) PCT No.: PCT/JP01/07357
§ 371 (c)(1),
(2), (4) Date: Feb. 27, 2003

(87) PCT Pub. No.: WO02/18586
PCT Pub. Date: Mar. 7, 2002

(65) Prior Publication Data
US 2004/0121346 A1    Jun. 24, 2004

(30) Foreign Application Priority Data

Aug. 30, 2000 (JP) ................................ 2000-261638
Mar. 2, 2001 (JP) ................................ 2001-058404

(51) Int. Cl.
*C12Q 1/68* (2006.01)
(52) U.S. Cl. .................................... 435/6.12; 536/24.33
(58) Field of Classification Search ............... 435/91.21, 435/6, 91.2; 536/22.1, 24.33; 530/350
See application file for complete search history.

(56) References Cited

U.S. PATENT DOCUMENTS

| | | | | |
|---|---|---|---|---|
| 5,489,527 | A | * | 2/1996 | Wilson ........................ 435/252.3 |
| 5,670,617 | A | * | 9/1997 | Frankel et al. ................. 530/300 |
| 6,303,337 | B1 | * | 10/2001 | Rothschild et al. ........... 435/69.1 |
| 6,623,920 | B1 | * | 9/2003 | Bee et al. .......................... 435/5 |

FOREIGN PATENT DOCUMENTS

| | | |
|---|---|---|
| EP | 0 485 608 A1 | 5/1992 |
| EP | 0 972 838 A1 | 1/2000 |
| EP | 1 221 481 A1 | 7/2002 |
| EP | 1 310 564 A1 | 5/2003 |
| EP | 1 316 617 A1 | 6/2003 |
| WO | WO 00/10604 | 3/2000 |
| WO | WO 00/24890 | 5/2000 |
| WO | WO 01/27260 | 4/2001 |

OTHER PUBLICATIONS

Martemyanov et al. Direct expression of PCR products in a cell-free transcription/translation system: synthesis of antibacterial peptide cecropin. FEBS Letters, vol. 414, pp. 268-270, 1997.*

Hanes, j. et al. In vitro selection and evolution of functional proteins by using ribosome display. PNAS, vol. 94, pp. 4937-4942, 1997.*
Miyagoe y et al. The androgen-dependent C4-Slp gene is driven by a constitutively competent promoter. PNAS, vol. 90, pp. 5786-5790, 1993.*
Miyagoe y et al. The androgen-dependent C4-Slp gene is driven by a constitutively competent promoter. PNAS, vol. 90, pp. 5786-5790, 1993.*
Makeyev et al., "Cell-free immunology: construction and in vitro expression of a PCR-based library encoding a single-chain antibody repertoire," *FEBS Letters, Elsevier Science Pub.* vol. 444, No. 2-3, pp. 177-180 (1999).
Yoshizawa et al., "Nuclease resistance of an extraordinarily thermostable mini-hairpin DNA fragment, D(GCGAAGC) and its application to in vitro protein synthesis," *Nucleic Acids Research*, vol. 22, No. 12, pp. 2217-2221 (1994).
Mitsuhashi et al., "Technical Report: Part 2. Basic Requirements for Designing Optimal PCR Primers," *Journal of Clinical Laboratory Analysis*, vol. 10, No. 5, pp. 285-293 (1996).
Martemyanov et al., "Direct expression of PCR products in a cell-free transcription/translation system: synthesis of antibacterial peptide cecropin," *FEBS Letters, Elsevier Science Pub.*, vol. 414, No. 2, pp. 268-270 (1997).
Nakano et al., "Cell-free Protein Synthesis Systems," *Bio. Advances*, vol. 16, No. 2, pp. 367-384 (1998).
Ueno, et al., "The 3'-untranslated region of mouse myelin basic protein gene increases the amount of mRNA in immortalized mouse oligodendrocytes," *Biochemical and Biophysical Research Communications*. vol. 204, No. 3, pp. 1352-1357 (1994).
Gallie et al., Identification of the motifs within the tobacco mosaic virus 5'-leader responsible for enhancing translation, *Nucleic Acids Research*, vol. 20, No. 17, pp. 4631-4638, (1992).
Wosten, "Eubacterial sigma-factors." *FEMS Microbiology Reviews*, vol. 22, No. 3, pp. 127-150 (1998).
Sawasaki et al., "A cell-free protein synthesis system for high-throughput proteomics," *Proceedings of the National Academy of Sciences of the USA*, vol. 99, No. 23, pp. 14652-14657 (2002).
Supplementary European Search Report for EP 01 95 8551 dated Sep. 20, 2004.

* cited by examiner

*Primary Examiner* — Prabha Chunduru
(74) *Attorney, Agent, or Firm* — Kilyk & Bowersox, P.L.L.C.

(57) ABSTRACT

Methods to construct a transcription template for cell-free protein synthesis that has a high translation template activity, using a 3'-side primer and a 5'-side primer for PCR are provided. The 5'-side primer for PCR has a sequence complementary to a base sequence containing at least a part of a promoter functional site from the 5'-end of a promoter and has a base sequence that does not contain a base sequence complementary to at least a part of a RNA polymerase-recognizing site of the 3'-end of the promoter. The other primer has a base sequence complementary to at least a part of the RNA polymerase-recognizing site of the 3'-end of the promoter and has a sequence that does not contain a base sequence complementary to at least a part of a promoter functional site from the 5'-end of the promoter.

4 Claims, 11 Drawing Sheets

(a)

cDNA Library (b) PCR products (c) Transcription product (mRNA)

(a)

cDNA library (b) PCR products (c) Transcription product (mRNA)

(a)

(b)

US 7,981,617 B2

SEQUENCE LISTING

```
<160> NUMBER OF SEQ ID NOS: 12

<210> SEQ ID NO 1
<211> LENGTH: 20
<212> TYPE: DNA
<213> ORGANISM: Artificial
<220> FEATURE:
<223> OTHER INFORMATION: Designed polynucleotide to construct a primer
      for PCR

<400> SEQUENCE: 1
agcgtcagac cccgtagaaa                                               20

<210> SEQ ID NO 2
<211> LENGTH: 21
<212> TYPE: DNA
<213> ORGANISM: Artificial
<220> FEATURE:
<223> OTHER INFORMATION: Designed polynucleotide to construct a primer
      for PCR

<400> SEQUENCE: 2
gcgtagcatt taggtgacac t                                             21

<210> SEQ ID NO 3
<211> LENGTH: 15
<212> TYPE: DNA
<213> ORGANISM: Artificial
<220> FEATURE:
<223> OTHER INFORMATION: Designed polynucleotide to construct a primer
      for PCR

<400> SEQUENCE: 3
ggtgacacta tagaa                                                    15

<210> SEQ ID NO 4
<211> LENGTH: 20
<212> TYPE: DNA
<213> ORGANISM: Artificial
<220> FEATURE:
<223> OTHER INFORMATION: Designed polynucleotide to construct a primer
      for PCR

<400> SEQUENCE: 4
gtcagacccc gtagaaaaga                                               20

<210> SEQ ID NO 5
```

```
<211> LENGTH: 16
<212> TYPE: DNA
<213> ORGANISM: Artificial
<220> FEATURE:
<223> OTHER INFORMATION: Designed polynucleotide to construct a primer
      for PCR based on the omega sequence of Tobacco Mosaic Virus

<400> SEQUENCE: 5
acattctaca actaca                                                         16

<210> SEQ ID NO 6
<211> LENGTH: 22
<212> TYPE: DNA
<213> ORGANISM: Artificial
<220> FEATURE:
<223> OTHER INFORMATION: Designed polynucleotide to construct a primer
      for PCR

<400> SEQUENCE: 6
gcatttaggt gacactatag aa                                                  22

<210> SEQ ID NO 7
<211> LENGTH: 20
<212> TYPE: DNA
<213> ORGANISM: Artificial
<220> FEATURE:
<223> OTHER INFORMATION: Designed polynucleotide to construct a primer
      for PCR

<400> SEQUENCE: 7
gggaagataa acagtatttt                                                     20

<210> SEQ ID NO 8
<211> LENGTH: 20
<212> TYPE: DNA
<213> ORGANISM: Artificial
<220> FEATURE:
<223> OTHER INFORMATION: Designed polynucleotide to construct a primer
      for PCR

<400> SEQUENCE: 8
ccctcgaggc gtgggccca                                                      20

<210> SEQ ID NO 9
<211> LENGTH: 38
<212> TYPE: DNA
<213> ORGANISM: Artificial
<220> FEATURE:
<223> OTHER INFORMATION: Designed polynucleotide to construct a primer
      for PCR
<220> FEATURE:
<221> NAME/KEY: misc_feature
<222> LOCATION: (20)..(38)
<223> OTHER INFORMATION: n is a, c, g, or t

<400> SEQUENCE: 9
acattctaca actacaatgn nnnnnnnnnn nnnnnnnn                                 38

<210> SEQ ID NO 10
<211> LENGTH: 19
<212> TYPE: DNA
<213> ORGANISM: Artificial
<220> FEATURE:
<223> OTHER INFORMATION: Designed polynucleotide to construct a primer
      for PCR
<220> FEATURE:
<221> NAME/KEY: misc_feature
<222> LOCATION: (1)..(19)
<223> OTHER INFORMATION: n is a, c, g, or t
```

```
<400> SEQUENCE: 10
nnnnnnnnnn nnnnnnnnn                                                    19

<210> SEQ ID NO 11
<211> LENGTH: 115
<212> TYPE: DNA
<213> ORGANISM: Artificial
<220> FEATURE:
<223> OTHER INFORMATION: Designed polynucleotide to construct a primer
      for PCR
<220> FEATURE:
<221> NAME/KEY: misc_feature
<222> LOCATION: (97)..(115)
<223> OTHER INFORMATION: n is a, c, g, or t

<400> SEQUENCE: 11
gcatttaggt gacactatag aagtattttt acaacaatta ccaacaacaa caacaaacaa        60
caacaacatt acattttaca ttctacaact acaatgnnnn nnnnnnnnnn nnnnn            115

<210> SEQ ID NO 12
<211> LENGTH: 89
<212> TYPE: DNA
<213> ORGANISM: Artificial
<220> FEATURE:
<223> OTHER INFORMATION: Designed polynucleotide to construct a primer
      for PCR

<400> SEQUENCE: 12
ggtgacacta tagaagtatt tttacaacaa ttaccaacaa caacaacaaa caacaacaac        60
attacatttt acattctaca actacaatg                                         89
```

TRANSCRIPTION TEMPLATE FOR CELL-FREE PROTEIN SYNTHESIS AND METHOD USING THE SAME

This application claims the benefit of earlier filed International Application No. PCT/JP01/07357 filed Aug. 28, 2001.

The application claims priority from Japanese Patent Application Nos. 2000-261638 and 2001-058404 which are incorporated herein by reference.

TECHNICAL FIELD

The present invention relates to the general design principle and the construction of a transcription template for synthesizing a translation template for use in the cell-free protein synthesis system from a gene, and a simple and efficient wheat embryo cell-free protein synthesis method using the transcription template.

BACKGROUND ART

At present, near the completion of the genome project, the focus of the research has rapidly shifted from gene structural analysis to gene functional analysis. It is believed that an intracellular protein does not function singly, but expresses its function cooperatively by interacting with various protein factors, nucleic acids, low-molecular species, and cell-membrane components, to biologically function as the sum of their interactions.

One of main subjects in the post-genome project is to analyze the relation between structure and function of various protein factor complexes. Results obtained from the analyses are expected to provide very important knowledge in wide areas covering basic biological studies, including structural biology and biochemistry, elucidation of the relation between the gene translation product and the etiology in the medical field, and the development of medicines.

As a method for carrying out, in vitro, the protein-synthesis reaction, a so-called "method for cell-free protein synthesis" or the like has been studied actively (Japan Patent Laid-Open Hei 6-98790, Japan Patent Laid-Open Hei 6-225783, Japan Patent Laid-Open Hei 7-194, Japan Patent Laid-Open Hei 9-291, Japan Patent Laid-Open Hei 7-147992). Methods can include components containing ribosomes or the like that can function as an intracellular original protein-translating device that are extracted from an organism, and a translation template, amino acids as substrate, energy sources, various ions, a buffer, and other effective factors that are added to the extract to synthesize a protein in vitro.

A cell extract or biological tissue extract for the protein synthesis for a reaction system for the cell-free protein system, i.e., a cell-free protein synthesis system, *Escherichia coli*, wheat embryo, rabbit reticulocyte, and so on are used. The cell-free protein synthesis system has properties comparable to a living cell with respect to "peptide synthesis rate" and "accuracy of translation reaction," and is advantageous because it does not require any complex chemical reaction step or cell culture step. Therefore, a practical system has been developed for it. Generally, however, an extract from cells of an organism has only a very unstable ability to synthesize a protein, so that protein synthesis efficiency is low. In addition, the quality of the cell extract is significantly reduced during storage. Therefore, the amount of a product obtained from the cell-free protein synthesis system is small and can be detected only by radioisotope labelling or the like. Thus, the cell-free protein synthesis system can not be used as a practical method for producing a protein.

Conventional efficient cell-free protein synthesis methods includes the consecutive cell-free protein synthesis method developed by Spirin et al. [Spirin, A., et al., (1993) Methods in Enzymology, 217, 123-142]. They added an expression plasmid having an inserted objective gene to a transcription-translation coupled cell-free protein synthesis system using a cell extract prepared from *Escherichia coli*, wheat embryo, or rabbit reticulocyte. Spirin et al. showed that the protein synthesis system permits efficiently synthesizing a protein, and they reported that the consecutive cell-free protein synthesis method using a transcription-translation coupled cell-free protein synthesis system using the *E. coli* extract provides about 1 mg of product per 1 ml of the reaction mixture.

However, the cell-free protein synthesis system using *Escherichia coli* demonstrates a high protein synthesis ability when the plasmid is in a circular form and using an expression plasmid into which the objective gene was inserted as a template. When a linear plasmid or a linear transcription template constructed by the polymerase chain reaction (PCR) method is used, however, the template DNA is degraded by a DNase in the contaminated *Escherichia coli* extract in a time as short as 2 h or so using *Escherichia coli* in the cell-free protein synthesis system. Therefore, the amount of protein that can be synthesized is reduced to the level of the conventional batch method, i.e., several tens μg or so per 1 ml of the reaction system. Thus, a cell extract or tissue extract, for the cell-free protein synthesis, prepared from *E. coli*, wheat embryo, or rabbit reticulocyte, by an existing method, is contaminated with nucleases, translation inhibition protein factors, proteases, and so on, and these contaminants deactivate or inactivate the translation reaction system during the protein synthesis reaction [Ogasawara, T., et al., (1999) EMBO J., 18, 6522-6531]. Therefore, any protein synthesis system using the cell extract or tissue extract gives a low synthesis efficiency, and the amount of protein obtained is small.

Recently, the inventors provided methods for solving the problems of these cell-free protein synthesis systems, as described in 1) cell extract preparation for cell-free protein synthesis and cell-free protein synthesis method (WO00/68412) and 2) template molecules having generality and efficient functions, and methods for using the same (WO01/27260). These methods remarkably (i.e., successfully) enhanced the protein synthesis efficiency with a wheat embryo cell-free protein synthesis system. The wheat embryo cell-free protein synthesis system developed by the inventors does not contain any nuclease or translation reaction inhibitors [Madin, K. et al., (2000) Proc. Natl. Acad. Sci. USA, 97, 559-564] (WO00/68412), and permits carrying out the efficient protein synthesis using a linear DNA as a transcription template, which has been difficult so far. All applications, patents, and publications mentioned above and throughout are incorporated in their entirety by reference herein.

On the other hand, a transcription template for the above efficient wheat embryo cell-free protein synthesis system is prepared by the template DNA construction method using an existing PCR method. In this method, primers were used which contain:

{1} the total region of a promoter site of a vector that is a recognition and binding site for RNA polymerase,
{2} a structure contributing to the translation amplification and the stabilization of mRNA, and {3} a part of ORF (open reading frame) of the objective gene, with {3} being downstream of {1} and {2}. Using these primers, the construction of a transcription template for the cell-free protein synthesis from the objective gene has been tried. Therefore, in an existing method for constructing a transcription template by the PCR method, in addition to the objective full-length transcription template, short DNA fragments having a promoter sequence are accumulated. Short DNA fragments accumulate because of non-specific DNA amplification occurring during the reaction. It is difficult to remove these DNA fragments. Therefore, if RNA is synthesized using "a PCR product using the above primers" as a transcription template, almost all of molecules obtained are low-molecular-weight RNAs that are non-specific transcription products of a short DNA. These RNA molecules contain RNA fragments having 5'-translation initiation sequence, and these are recognized as mRNAs and translated. As a result, in addition to translation products of the objective gene, a large amount of low-molecular-weight translation products are formed, which results in the reduction of the yield and purity of the objective translation product.

Thus, an existing method for constructing a translation template using a transcription template constructed by designing and using a 5'-end side primer containing a base sequence complementary to the full-length promoter had the following big faults:
1) the transcription efficiency of the objective gene is very low, and
2) the method gives a translation template containing many noises (errors).

In addition, it is believed that even with the transcription template constructed, the efficient protein synthesis by the transcription-translation coupled method using the conventional batch wheat embryo cell-free protein synthesis system was impossible because the optimal magnesium concentration for the transcription reaction and for the translation reaction are quite different from each other. Moreover, the low efficiency of the cell-free protein synthesis system is affected by four ribonucleoside triphosphates (4NTPs) that are remnants of transcription substrates and pyrophosphate that is a by-product, which strongly inhibit the translation reaction.

With the progress of the genome project, many gene structures have been elucidated now, and several tens of thousands of cDNA clones have been isolated. As the first step for the analyses of functions and structures of genes in the basic and applied sciences in the 21st century, for the proteome analysis, and for the creation of medicines, it is necessary to simply and efficiently synthesize proteins that are gene products from the large amount of genes. The elemental technology to do so requires {1} designing an mRNA keeping a high translation template activity, {2} the transcription template-constructing technique for synthesizing an mRNA, and {3} a simple cell-free translation technique using the transcription template-constructing technique.

DISCLOSURE OF THE INVENTION

One aspect of the present invention provides a base sequence of a 3'-end side primer. The primer can be used when a transcription template for preparing a translation template molecule having a 3'-end untranslated sequence, used for cell-free protein synthesis, is prepared by PCR. The base sequence of the 3'-end side primer can comprise:
a) a base sequence containing a base sequence capable of forming a complementary strand with a base sequence present between a transcription terminator sequence of a marker gene, such as a drug resistance gene, of a vector into which a gene was inserted and a sequence containing a part of Ori (1),
b) the base sequence shown by sequence no. 1 in the sequence listing (2),
c) a base sequence containing a main part of the base sequence shown by sequence no. 1 in the sequence listing (3),
d) a base sequence hybridizable to a base sequence selected from a group consisting of (1), (2), and (3) under stringent conditions, or
e) a base sequence complementary thereto.

One aspect of the present invention provides a base sequence of a 5'-end side primer used when a transcription template for preparing a translation template molecule, used for cell-free protein synthesis, is prepared by PCR. The base sequence of 5'-end side primer can comprise:
a) a base sequence containing a base sequence partially complementary to the promoter sequence of RNA polymerase (4),
b) a base sequence shown by sequence no. 2 or 3 in the sequence listing (5),
c) a base sequence containing the base sequence shown by sequence no. 3 in the sequence listing (6),
d) a base sequence containing the main part of "one of base sequence (5) and (6)" (7),
e) a base sequence hybridizable to one base sequence selected from a group consisting of base sequences (4)-(7) under stringent conditions (8), or
f) a base sequence complementary to one of these base sequences (4)-(8).

One aspect of the present invention provides a method for constructing a transcription template by PCR using two polynucleotides (A) and (B) having different base sequences as the base sequence of a 5'-end side primer used when the transcription template for preparing a translation template molecule used for the cell-free protein synthesis is prepared by PCR. The base sequences of the two primers for PCR satisfy the condition that any transcription does not occur from a DNA constructed with one of the primers. One of the primers is a polynucleotide (A) that has a sequence complementary to a base sequence containing at least a part of a promoter functional site from the 5'-end of a promoter and has a base sequence that does not contain a base sequence complementary to at least a part of the RNA polymerase-recognizing site at 3'-end of the promoter. The other of the primers is a polynucleotide (B) that has a sequence complementary to a base sequence containing at least a part of the promoter functional site from the 3'-end of a promoter and has a base sequence that does not contain a base sequence complementary to at least a part of the RNA polymerase-recognizing site at the 5'-end of the promoter.

One aspect of the present invention provides a method for constructing a transcription template, wherein a polynucleotide consists of a base sequence of polynucleotide (B), GA or GAA sequence, a base sequence giving the translational amplification of an mRNA, the translation initiation codon ATG, and/or a base sequence complementary to "a part of ORF (open reading frame)" or "upstream of ORF (not containing ORF)" of the objective gene in this order, is used.

One aspect of the present invention provides a method for constructing a transcription template, wherein {1} a histidine tag or GST (glutathione S-transferase) and/or {2} a base sequence for synthesizing a tag such as myb or epitope is inserted between "the initiation codon" and "ORF" of the translation part of the polynucleotide.

One aspect of the present invention provides a method for constructing, by PCR, a transcription template for preparing a translation template molecule for the cell-free protein synthesis method, wherein
{1} a polynucleotide having a base sequence shown by sequence no. 2 in the sequence listing,
{2} a polynucleotide having a base sequence obtained by linking Ω sequence derived from tobacco mosaic virus and the translation initiation codon ATG to the base sequence shown by sequence no. 3 in the sequence listing, or {3} a polynucleotide having a base sequence obtained by linking the translation initiation codon ATG and the 5'-end side base sequence of ORF being inherited to the gene to be transcribed, in this order, to the base sequence shown by sequence no. 5 in the sequence listing, is used for the 5'-end side primer of the transcription template, and wherein a polynucleotide having the base sequence shown by sequence no. 1 in the sequence listing is used for the 3'-end side primer of the transcription template.

One aspect of the present invention provides a primer set containing the following four constituents for preparing a transcription template by the PCR method:

(1) a polynucleotide (A) that has a sequence complementary to a base sequence containing at least a part of the promoter functional site from the 5'-end of a promoter as the 5'-end side primer, and has a base sequence that does not contain a base sequence complementary to at least a part of the RNA polymerase-recognizing site of 3'-end side of the promoter, (2) a polynucleotide (B) that has a sequence complementary to a base sequence containing at least a part of the RNA polymerase-recognizing site from the 3'-end of the promoter, and has a base sequence that does not contain a base sequence complementary to at least a part of the promoter functional site of the 5'-end side of the promoter, (3) a polynucleotide (C) obtained by linking a base sequence capable of annealing polynucleotide B, the translation initiation codon ATG or a base sequence complementary to a base sequence of a part of ORF (open reading frame) or upstream of an ORF (not containing the ORF) of the objective gene, in this order, and (4) a polynucleotide containing a base sequence capable of forming a complementary strand with a base sequence present between a transcription terminator sequence of a marker gene, such as a drug resistance gene, of vector into which a gene was inserted as the 3'-end side primer and a sequence containing a part of Ori.

One aspect of the present invention provides the primer set wherein polynucleotide B is a polynucleotide obtained by linking a base sequence complementary to a base sequence containing at least a part of an RNA-polymerase recognizing site from the 3'-end of the promoter, a base sequence that does not contain a base sequence complementary to at least a promoter functional site of the 5'-end side of the promoter, GA or GAA sequence, a sequence giving the translational amplification of an mRNA in the downstream, the translation initiation codon ATG or a sequence complementary to the base sequence upstream of the ORF (not containing the ORF) of the objective gene, in this order.

One aspect of a primer set of the present invention is constituted by the following combinations: a polynucleotide having a base sequence shown by sequence no. 2 in the sequence listing, a polynucleotide having a base sequence obtained by linking the Ω sequence derived from the tobacco mosaic virus and the translation initiation codon ATG to the base sequence shown by sequence no. 3 in the sequence listing, and a polynucleotide having a base sequence obtained by linking the translation initiation codon ATG and 5'-end side base sequence of ORF being inherited to a gene to be transcribed, in this order, to the base sequence shown by sequence no. 5 in the sequence listing, and a 3'-end side primer containing a polynucleotide having a base sequence shown by sequence no. 1 in the sequence listing. The resultant compound is a primer set for preparing, by the PCR, a transcription template for constructing a translation template molecule for use in the cell-free protein synthesis method.

One aspect of the present invention provides a transcription template for efficiently synthesizing an mRNA for use in the cell-free protein synthesis, wherein the transcription template is prepared by any one of the construction methods.

One aspect of the present invention provides a transcription template for efficiently synthesizing an mRNA for the cell-free protein synthesis, wherein the transcription template was synthesized by the PCR using any one of the primer sets.

One aspect of the present invention provides a cell-free protein synthesis method using, as a translation template, an mRNA transcribed from a transcription template prepared by any one of the construction methods or from any one of the transcription templates.

One aspect of the present invention provides the cell-free protein synthesis method, wherein an mRNA is synthesized and then purified by gel filtration.

One aspect of the present invention provides a transcription-translation consecutively diluting cell-free protein synthesis method, wherein a transcription template is prepared by any one of the construction methods, the transcription reaction is carried out using a solution for the transcription, and a reaction mixture for the cell-free protein synthesis is added to reduce at least the concentration of magnesium in the reaction mixture to an optimal concentration for the translation to prolong the lifetime of the translation reaction.

One aspect of the present invention provides a transcription-translation coupled diluting cell-free protein synthesis method, wherein {1} a transcription template is prepared by any one of the construction methods, {2} the transcription reaction is carried out using a reaction mixture for the cell-free protein synthesis, {3} a diluent is added to the reaction mixture after the step {2}, {4} at least the concentration of magnesium in the reaction mixture is reduced to optimal concentration for the translation, {5} the concentration of the transcription substrate and of the transcription byproduct in the reaction mixture is reduced, and {6} the lifetime of the translation reaction is prolonged.

One aspect of the present invention provides a transcription-translation consecutively diluting cell-free protein synthesis method, wherein {1} a cDNA is added to a reaction vessel, {2} a transcription template is prepared in the reaction vessel by any one of the methods for constructing a transcription template, {3} a transcription reaction is carried out with a reaction mixture, for the transcription, containing an RNA polymerase and four ribonucleoside triphosphates, {4} a reaction mixture for the cell-free protein synthesis is further added after the step {3}, {5} the concentration of at least magnesium in the reaction mixture is reduced to an optimal concentration, and {6} the translation reaction is carried out.

One aspect of the present invention provides a transcription-translation consecutively diluting cell-free protein synthesis method, wherein {1} a cDNA is added to a reaction vessel, {2} a transcription template is prepared in the reaction vessel by any one of the methods for constructing a transcription template, {3} a transcription reaction is carried out with a reaction mixture, for the cell-free protein synthesis, containing an RNA polymerase and four ribonucleoside triphosphates, {4} a diluent is added for dilution after the step {3}, {5} at least the concentration of magnesium in the reaction mixture is reduced to an optimal concentration, and {6} the translation reaction is carried out.

One aspect of the present invention provides any one of the cell-free protein synthesis methods, wherein the concentration of magnesium is reduced to about 1 mM to about 6 mM.

One aspect of the present invention provides any one of the cell-free protein synthesis methods, wherein the transcription reaction is carried out at about 30° C. to about 45° C., and the translation reaction is carried out at about 20° C. to about 30° C.

One aspect of the present invention provides any one of the cell-free protein synthesis methods, wherein a wheat embryo extract is used.

BRIEF DESCRIPTION OF DRAWINGS

FIG. 1a illustrates the structure of pEU derived from pUC19 into which the GFP gene is inserted as the ORF and the primer for constructing a transcription template by the PCR method. FIG. 1b illustrates a transcription product by SP6 RNA polymerase. FIG. 1c illustrates the protein synthesis using the incorporation of $^{14}$C-leucine as an index in a batch wheat embryo cell-free protein synthesis system using these mRNAs. 'Cap' in the figure is an mRNA having Cap synthesized by adding 7mGpppG to 5'-end of the mRNA; 'Circular' is an mRNA constructed using a circular plasmid as a transcription template.

FIG. 2a illustrates a template plasmid for constructing a transcription template and a primer for the PCR. FIG. 2b illustrates main PCR products. FIG. 2c illustrates an RNA molecular species estimated to be transcribed by SP6 RNA polymerase, from a transcription template obtained as PCR products.

FIG. 5a illustrates a plasmid that is a template for constructing a transcription template and primers for PCR. FIG. 5b illustrates main PCR products. FIG. 5c illustrates an RNA molecular species estimated to be transcribed, from a transcription template obtained as a PCR product, by SP6 RNA polymerase.

FIG. 9a illustrates time courses of the incorporation of $^{14}$C-leucine into proteins by the conventional batch method (●-●) and the dilution method (○-○), with the radioactivity counts of Y-axis being expressed per the same volume of embryo extract. FIG. 9b illustrates an autoradiogram of protein obtained.

FIG. 10a illustrates the time course of the incorporation of $^{14}$C-leucine into proteins. An RNA synthesis substrate concentration in the transcription reaction step was 1.5 mM (□-□, small symbol), 2.5 mM (□-□, middle symbol), or 3.0 mM (□-□, large symbol). Results of the conventional batch method (●-●) and the dilution method (○-○) are also shown. FIG. 10b illustrates an autoradiogram of proteins obtained.

BEST MODE FOR CARRYING OUT THE INVENTION

Figure 1:
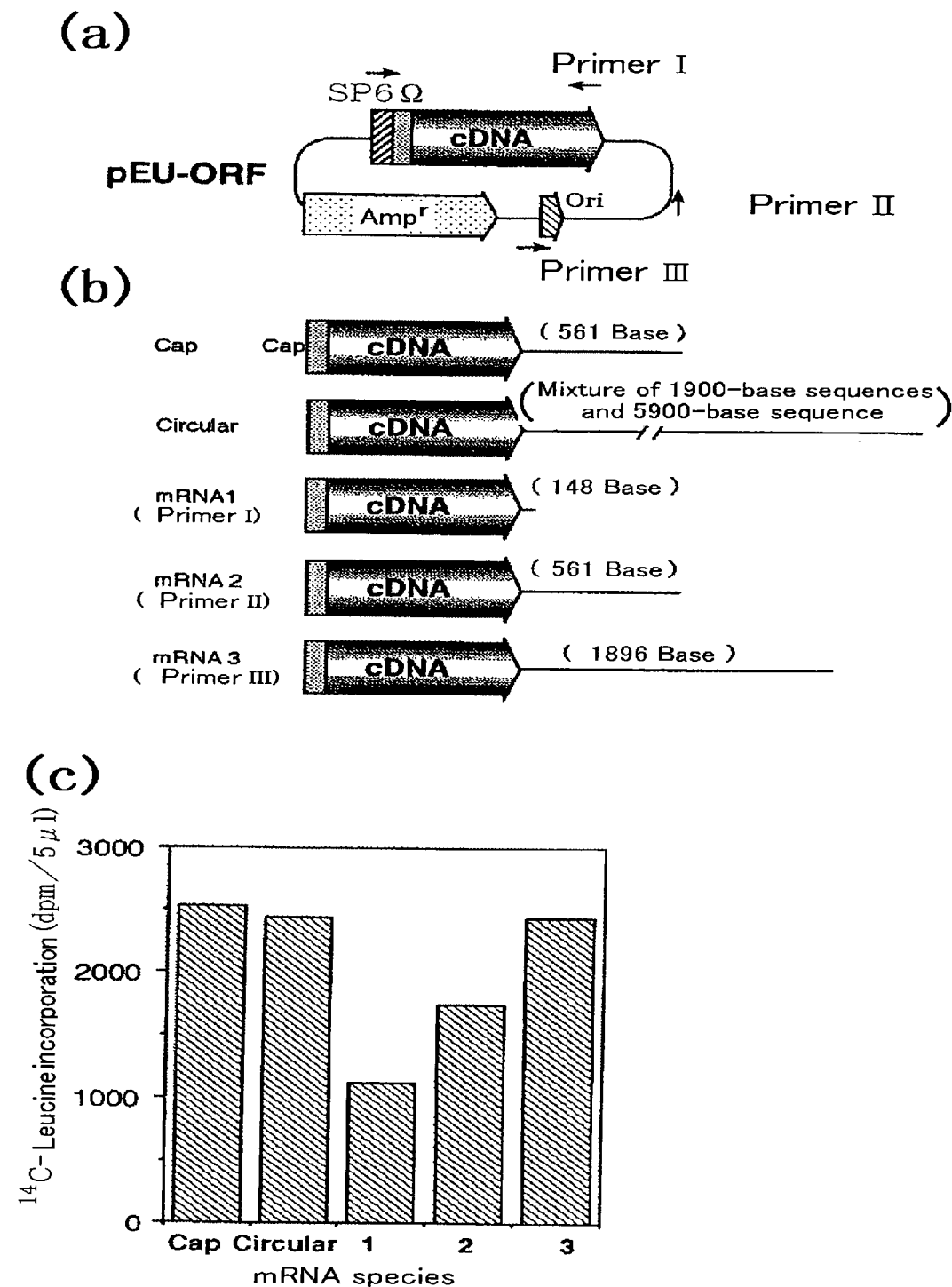
FIG. 1 illustrates the designing of a primer for obtaining, by the PCR, a transcription template for an mRNA that has 3'-end untranslated sequence and a high translation template activity in Example 1.

Among cell-free protein synthesis systems that have been developed so far, one using a wheat-embryo extract has a weaker nuclease activity, a more stable translation activity, and a higher property than that of an *Escherichia coli* extract [Madin K. et al., (2000) Proc. Natl. Acad. Sci. USA, 97, 559-564]. Therefore, it is possible to efficiently synthesize proteins by the transcription-translation coupled method using a plasmid as a template (WO00/68412).

The present invention is described below by providing, as examples, a wheat embryo cell-free protein synthesis system and methods for designing and constructing a transcription template that can function in the system. The basic principle of the present invention is not limited to these examples, but can be applied to cell-free protein synthesis systems using cell extracts derived from other microorganisms and animal cells and for designing and constructing a transcription template using one of the systems.

Structures of Primers for Constructing Transcription Template

Applicants developed 5'- and 3'-end untranslated structures of an mRNA necessary for a high translation template activity using a cell-free protein synthesis system using a wheat embryo extract that was already stabilized and made efficient, and the structures were published [WO01/27260]. In particular, it was elucidated that adding a long-chain 3'-end untranslated structure to an mRNA is very effective to enhance the efficiency of a cell-free protein synthesis reaction.

(1) Construction of 3'-End Side Primer

In order to construct, by the PCR method, a transcription template of an mRNA that is effective to enhance the translation template activity and has a 3'-end untranslated structure as short as possible, PCR was carried out using a plasmid, as a template, into which jelly fish green fluorescent protein (GFP) gene [see FIG. 1*a*] was inserted as a model gene.

For a 5'-end side primer for amplifying a transcription template of GFP gene by the PCR method, a polynucleotide having the following base sequence was used:

5' GCATT TAGGT GACAC TATAG AA 3'-SEQ. ID NO. 6

For a 3'-end side primer, the following three primers (see FIG. 1) were used for comparison:

Primer I: 5' GGGAA GATAA ACAGT ATTTT 3'-SEQ. ID NO. 7 (for transcripting mRNA 1)
Primer II: 5' CCCTC GAGGC GTGGG CCCCA 3'-SEQ. ID NO. 8 (for transcripting mRNA2)
Primer III: 5' AGCGT CAGAC CCCGT AGAAA 3'-SEQ. ID NO. 1 (for transcripting mRNA3)

Primer III (sequence no. 1 in the sequence listing) is a base sequence capable of forming a complementary strand with a base sequence present between the transcription terminator sequence of a drug resistance marker gene (Amp$^r$ in FIG. 1) and a DNA replication origin base sequence (Ori). Primers I and II are reference sequences.

Examinations revealed that primer III is the best for a 3'-end side primer for constructing the transcription template and can give a transcription template suitable for obtaining an mRNA having a high translation template activity.

Primer III is a preferable 3'-end side primer for synthesizing, by PCR, a base sequence to function as a transcription template for the 3'-end untranslated sequence of a translation template molecule for the cell-free protein synthesis method. The 3'-end side primer is not limited to Primer III. A primer having a base sequence (e.g., a base sequence containing a base sequence that can form a complementary strand to a base sequence being inherited to each vector) present between the transcription terminator sequence of a marker gene, such as a drug resistance gene, of a vector into which a gene was inserted and the sequence partially containing DNA replication origin base sequence (Ori) can be used for the primer. The primer need not have a specific base sequence. The primer can have the following base sequences:

1) base sequences containing the main part of the base sequence shown by sequence no. 1 in the sequence listing,
2) base sequences that can hybridize to these sequences under stringent conditions, or
3) base sequences complementary to these, wherein "hybridize . . . under stringent conditions" means that a positive hybridization signal is observed even after 1) being heated in a solution containing 6×SSC, 0.5% SDS, and 50% formamide at 42° C., followed by
2) being washed in a solution containing 1×SSC and 0.5% SDS at 68° C.

Such a base sequence can be obtained, for example, by the method described, for example, in "Molecular Cloning: A Laboratory Manual" (Cold Spring Harbor Laboratory, 1989).

Using the above 3'-end side primer according to the present invention permits simply obtaining, by PCR, a transcription template of an mRNA that is effective for enhancing the translation template activity and has a 3'-end untranslated structure that is as short as possible. It is often difficult to amplify a long-chain DNA by the PCR method because of the properties of the reaction. Therefore, the present invention has made it possible to construct, by the PCR method, a transcription template of an mRNA to which a long-chain untranslated region was added. The construction has been difficult so far.

(2) Designing and Constructing a Transcription Template Using a Conventional 5'-End Side Primer by the PCR Method For model genes, three cDNAs derived from the rat liver (encoding proteins having molecular weights of 18 kDa, 25 kDa, and 44 kDa) and a cDNA encoding a GFP (protein having a molecular weight of 27 kDa) were used. Then, plasmid pUC19 into which the above cDNA was inserted was used.

For the 5'-end side primer in the first-step PCR, primer 3 described below, which has a base sequence (5' ACA TTC TAC AAC TAC A 3'-SEQ. ID NO. 5; sequence no. 5 in the sequence listing) derived from the Ω sequence of tobacco mosaic virus, was used. The underlined ATG in the base sequences described below is the initiation codon of ORF, and X represents a 5'-end side base sequence of ORF being inherited to the gene. Although a base sequence consisting of 19 consecutive nucleotides from the 5'-end of each of the above cDNA was used as a 5'-end side base sequence of ORF being inherited to the gene as shown here, the number of X can be from about 13 to about 30.

Primer 3: 5' ACATT CTACA ACTAC A<u>ATG</u>X XXXXX XXXXX XXXXX XXX 3'-SEQ. ID NO. 9

For the 3'-end side primer for the PCR, primer III (sequence no. 1 in the sequence listing) for transcripting the above mRNA3 was used.

For the 5'-end side primer for the second-step PCR, the following two primers were used:

1) the following primer 1 corresponding to all the region of the promoter base sequence of an RNA polymerase:

Primer 1: 5' GCATT TAGGT GACAC TATAG AA 3'-SEQ. ID NO. 6

2) followed by the following sequence (primer 2) containing Ω sequence and the 5'-end side base sequence (XXXXX XXXXX XXXXX XXXX,-SEQ. ID NO. 10-19 bases) of the ORF being inherited to the gene:

Primer 2: 5' GCATT TAGGT GACAC TATAG AAGTA TTTTT ACAAC AATTA CCAAC AACAA CAACA AACAA CAACA ACATT ACATT TTACA TTCTA CAACT ACA<u>ATG</u>XXXX XXXXX XXXXX XXXXX 3'-SEQ. ID NO. 11

Although a base sequence consisting of 19 consecutive nucleotides from the 5'-end of each of the above cDNA was used as a 5'-end side base sequence of ORF being inherited to the gene as shown here, the number of X can be from about 13 to about 30.

For the 3'-end side primer for the PCR, the following primer IV (sequence no. 4 in the sequence listing) was used. Primer IV was designed and prepared by shifting the base sequence of the above primer III (sequence no. 1 in the sequence listing), for mRNA3 transcription on the promoter sequence, by 3 bases:

Primer IV: 5' GTCAG ACCCC GTAGA AAAGA 3'-SEQ. ID NO. 4

(3) Designing and constructing a transcription template using promoter sequence-divided type primers In order to design and construct a transcription template giving a low background, for the 5'-end side primer, two primers having different base sequences each partially complementary to the promoter sequence of RNA polymerase were designed and used. One of the primers is polynucleotide A (e.g., primer {1} below) that has a sequence complementary to a base sequence containing at least a part of the promoter functional site from the 5'-end of the promoter but does not have a base sequence complementary to at least a part of the RNA polymerase-recognition site at the 3'-end of the promoter. The other one of the primers is polynucleotide B (e.g., primer {2} below) that has a base sequence complementary to a base sequence containing at least a part of the RNA polymerase-recognizing site from the 3'-end of the promoter but does not have a base sequence complementary to at least the promoter functional site of the 5'-end of the promoter. That is, each of the above two primers is a promoter sequence-divided type primer having a base sequence complementary to a different part of a promoter base sequence. The two promoter sequence-divided type primers have such a property that the transcription occurs with a DNA constructed by the PCR using both of these primers, but the transcription does not occur with a DNA constructed by the PCR using one of these primers. Promoter sequence-divided type primers {1} and {2} given here as an example are SP6 promoter sequence-divided type primers. Promoter sequence-divided type primers according to the present invention are not limited to these, but they can be prepared based on base sequences of various promoters.

Primer {1}: 5' GCGTA GCATTTAGGTGACACT 3'-SEQ. ID NO. 2 (sequence no. 2 in the sequence listing) (the underlined part is complementary to the 5'-end side of SP6 promoter, but lacks ATA complementary to the 3'-end side), Primer {2}: 5' GGTGACACTATAGAA-SEQ. ID NO. 3 (sequence no. 3 in the sequence listing) (the underlined part is complementary to the 3'-end side of SP6 promoter, but lacks ATTTA complementary to the 5'-end side), Ω sequence (71 bases), and ATG derived from the inserted gene, serially in this order, and Primer {3}: the same as primer 3 above.

A model gene obtained by integrating three cDNAs derived from the rat liver and a cDNA encoding GFP to pUC19 was used. For the 5'-end side primer in the first-step PCR, a primer (38 bases total) containing the sequence 5' ACATT CTACA ACTAC A 3'-SEQ. ID NO. 5 (sequence no. 5 in the sequence listing), a base sequence derived from Ω sequence, and a sequence complementary to the 5'-end part of ORF consisting of 22 bases initiating with the translation initiation codon ATG of the objective gene, in this order, was used. For the 3'-end side primer in the first-step PCR, primer III (sequence no. 1 in the sequence listing) for the mRNA3 transcription was used. In addition, for the 5'-end side primers in the second-step PCR, primers {1} and {2} were used. For the 3'-end primer in the second-step PCR, the above primer IV (sequence no. 4 in the sequence listing) was used, with a ({1}:{2}:IV) molar ratio of primers being 100:1:100. It is not necessary to carry out the PCR in two steps. Carrying out the PCR in one step does not change the essence of the present invention at all.

A transcription template constructed using the 5'-end side primer for the above conventional method and a transcription template constructed using the above promoter-divided type 5'-end side primer according to the present invention were compared to each other with respect to the synthesis efficiency of the translation template and the efficiency of the cell-free protein synthesis. As a result, in case promoter-divided type primers were used, both efficiencies were high.

A promoter sequence-divided type primer, such as primers {1} and {2}, is useful for constructing, by PCR, the translation template of an mRNA that can be used for the cell-free protein synthesis system. The primer has a 5'-end untranslated sequence and a high translation activity without isolating an mRNA having an objective size, after the transcription reaction. That is, mRNAs transcribed from the transcription template, obtained by PCR using promoter sequence-divided type primers, contains substantially no short mRNAs that are non-specifically formed and are contaminated. This is distinct from mRNAs obtained by using the conventional primers. A non-specific short mRNA works as a strong inhibitor for producing an objective protein and remarkably reduces the synthesis yield in the cell-free protein synthesis method. If the translation template according to the present invention is used, however, the reaction is not affected by the short mRNA. Therefore, the cell-free protein synthesis can be efficiently carried out. In addition, mRNAs transcribed from a transcription template obtained by the PCR method using promoter sequence-divided type primers can be used for the cell-free protein synthesis system without isolating an mRNA having the objective size after the synthesis. Therefore, the synthesis of the mRNA and the synthesis of a protein from the mRNA can be simply carried out.

Base sequences of the 5'-end side primer for the PCR for constructing a DNA base sequence to be a transcription template for synthesizing a translation template molecule for the above cell-free protein synthesis method are as follows:

1) a base sequence containing a base sequence partially complementary to the promoter sequence of an RNA polymerase, 2) a base sequence shown by sequence no. 2 or sequence no. 3 in the sequence listing, 3) a base sequence containing the base sequence shown by sequence no. 3, 4) a base sequence containing the main part of these base sequences, 5) a base sequence hybridizable to these base sequences under stringent conditions, and 6) base sequences complementary to these base sequences.

Using the above 5'-end primer according to the present invention permits more simply obtaining, by the PCR method, a transcription template while minimizing the amounts of background transcription products. In case a transcription template is constructed using the above 5'-end primer, for example, two primers consisting of different base sequences that are base sequences of primers for PCR of the above 5'-end, can be used. In addition, it is preferable to use one of the above 3'-end side primer according to the present invention for the 3'-end side primer.

The above two 5'-end side primers satisfy the condition that the transcription does not occur from a DNA constructed from only one of the two primers. One of the two primers is polynucleotide (A). Polynucleotide (A) has a sequence complementary to a base sequence containing at least a part of the promoter functional site from the 5'-end of the promoter, but does not have a base sequence complementary to at least a part of an RNA polymerase-recognizing site at the 3'-end of the promoter. In addition, the other one of the two primers is polynucleotide (B). Polynucleotide (B) has a sequence complementary to a base sequence containing at least a part of an RNA polymerase-recognizing site from the 3'-end of the promoter, but does not have a base sequence complementary to at least the promoter functional site at the 5'-end of the promoter. It is preferable that the primers have these properties.

In addition, the base sequence of the above polynucleotide (B) can be a polynucleotide having a base sequence prepared by:
1) further inserting GA or GAA sequence into the base sequence, followed by linking, on the downstream side,
2) a sequence giving the translation amplification of an mRNA, and
3) translation initiation codon ATG and/or a sequence complementary to the base sequence of a part of ORF (open reading frame) of the objective gene or a sequence upstream (5'-end side) of ORF (not containing ORF).
Base sequences that give the translation amplification of an mRNA are, for example, 1) $\Omega$ sequence of tobacco mosaic virus, 2) a base sequence derived from a leader sequence of alfalfa mosaic virus (AMV), 3) AMV-$\Omega$ sequence obtained by serially linking (1) and (2), and 4) a 29-base $\Omega$ sequence derived from the $\Omega$ sequence. However, they are not limited to these sequences as long as they give the translation amplification.

Optionally, for the above 5'-end side primer, three polynucleotides containing the above polynucleotide (A), the above polynucleotide (B), and a polynucleotide (C) prepared by linking a base sequence capable of annealing polynucleotide (B), translation initiation codon ATG, and/or a base sequence complementary to the base sequence of a part of ORF or a sequence upstream of ORF (5'-end side, not containing ORF) of the objective gene, in this order, can be used. A part of the ORF (translation frame) of the objective gene is a base sequence consisting of from about 13 to about 30 consecutive bases from the 5'-end of the ORF. Although polynucleotide (B) has a base sequence complementary to a base sequence containing at least a part of the RNA polymerase-recognizing site from the 3'-end of a promoter, the polynucleotide can be a polynucleotide having a base sequence obtained by linking a base sequence not having a base sequence complementary at least to the promoter functional site of the 5'-end side of the promoter, GA or GAA sequence, a sequence giving the translation amplification of an mRNA, and the translation initiation codon for the mRNA or a sequence complementary to the base sequence of a part of ORF of the objective gene or a sequence upstream of ORF (5'-end side, not containing ORF), in this order.

In addition, between the initiation codon of the translation part of the above 5'-end side primer and ORF, a tag such as a histidine tag, glutathione S-transferase (GST), and myb or a base sequence for synthesizing an epitope, can be inserted. By using a transcription template prepared using such a primer, the above tag or epitope is added to the finally obtained translation product as one for purifying the translation product or for marker purposes.

A combination consisting of the above two primers or three primers can be used as a 5'-end side primer that can be generally used for preparing transcription templates for various genes. A combination of primers will be called a "primer set" hereafter. In addition to the above primer set, a marker gene (e.g., a primer set obtained by combining polynucleotides having base sequences capable of forming a strand complementary to a base sequence present between a transcription terminator sequence, such as a drug resistance gene, and a sequence partially containing ORF) of a vector into which a gene was inserted can be used as a 3'-end side primer of a primer set that can be generally used for preparing transcription templates of various genes by the PCR.

(Transcription-Translation Coupled Dilution Protein Synthesis Method and Transcription-Translation Consecutive Dilution Protein Synthesis Method)

Using a transcription template obtained by the PCR method using primers according to the present invention permits simply and efficiently synthesizing a protein. For example, an mRNA "as a template" synthesized using a transcription template constructed by the above principle and method is added to a reaction mixture for the cell-free protein synthesis containing a wheat embryo extract in an amount sufficient for the protein synthesis to carry out the cell-free protein synthesis. The above synthesis reaction continues for a longer time than the protein synthesis using an mRNA synthesized by the conventional method. For synthesizing an mRNA from the transcription template, a well-known transcription reaction can be used. The cell-free protein synthesis is also carried out by an already-known method [Madin K. et al., (2000) Proc. Natl. Acad. Sci. USA, 97, 559-564] (WO00/68412). Moreover, using an mRNA that was synthesized and purified by a method such as gel filtration permits enhancing the synthesis efficiency of a protein.

In addition, carrying out the protein synthesis by combining a transcription template obtained by the PCR method using primers according to the present invention to the already reported transcription-translation coupled cell-free protein synthesis method [WO00/68412] permits avoiding the complexity of adding an mRNA prepared by the transcription to the cell-free protein synthesis system. For the transcription-translation coupled wheat embryo cell-free protein synthesis method using the transcription template, the transcription reaction is first carried out under conditions suitable for the transcription reaction. The transcription reaction is carried out preferably at about 30° C. to about 45° C., more preferably at about 35° C. to about 40° C. Then, the condition of the reaction mixture is changed to one suitable for the translation reaction by adding an appropriate diluent to carry out the protein synthesis. The temperature for the translation reaction depends on the protein synthesized, and is preferably about 20° C. to about 30° C. Moreover, the diluent can be a buffer that is prepared by supplementing energy sources and amino acids necessary for the translation reaction, and is suitable for the translation reaction. In addition, the diluent is added so that at least the concentration of magnesium in the reaction mixture can be the optimal concentration for the translation, preferably about 1 mM to about 6 mM. Adding a diluent permits reducing the concentrations of transcription substrates and transcription by-products contained in the reaction mixture at the same time. Hence, the lifetime of the protein synthesis reaction can be prolonged, and the synthesis efficiency is enhanced.

For the transcription-translation coupled dilution cell-free protein synthesis method, for example, first of all, a reaction mixture that contains a wheat embryo extract (concentration, 200 $A_{260nm}$ units/ml) at 48% (v/v) and has the following composition (final concentration): 1,000 units/ml ribonuclease inhibitor (RNAsin), 30 mM HEPES-KOH (pH 7.6), 95 mM potassium acetate, 16 mM magnesium acetate, 2.85 mM dithiothreitol, 0.5 mg/ml creatine kinase, 2.5 mM ATP, 2.5 mM GTP, 2.5 mM UTP, 2.5 mM CTP, 1500 units/ml SP6 RNA polymerase, 16 mM creatine phosphoric acid, 1.48 mM spermidine, 0.3 mM each of twenty L-type amino acids, and 25 µg/ml DNA as a transcription template, is prepared. Then, the reaction mixture is incubated at 30° C. for 3 h for the transcription reaction. After the reaction, the reaction mixture is diluted with a diluent, for example, having the following composition: 30 mM HEPES-KOH (pH 7.6), 95 mM potassium acetate, 0.4 mM magnesium acetate, 2.85 mM dithiothreitol, 0.94 mM ATP, 0.25 mM GTP, 16 mM creatine phosphoric acid, 0.380 mM spermidine, and 0.3 mM each of twenty L-type amino acids. After the dilution, the reaction mixture has the following composition (main composition): 8% (v/v) wheat embryo extract (original extract has 200 $A_{260nm}$ units/ml), 30 mM HEPES-KOH (pH 7.6), 95 mM potassium acetate, 3 mM magnesium acetate, 1.2 mM ATP, and so on, wherein concentrations of GTP, UTP, and CTP after the dilution are not calculated because their amounts consumed during the transcription reaction are unknown.

For the above transcription-translation coupled dilution cell-free protein synthesis method, the wheat embryo extract from cell extract necessary for the translation reaction exists in the reaction mixture ab initio, so that the extract exists also in the transcription reaction. However, it is not necessary for the extract to exist in the reaction mixture ab initio. In addition, when a diluent is added after the synthesis of mRNA, the extract can be added to the cell-free protein synthesis system together with the diluent as a mixture or in separate solutions so that the final concentration of the extract can be a level suitable for the translation reaction. This method is called "transcription-translation consecutively diluting cell-free protein synthesis method" herein.

The transcription-translation coupled and transcription-translation consecutive dilution cell-free protein synthesis methods do not include complex procedures, i.e., simple. In addition, these methods permit efficiently synthesizing a protein in a cell-free system directly using a transcription template constructed by the PCR method. Moreover, synthesizing an objective gene product as a fused protein with a histidine tag or a glutathione S-transferase permits efficiently purifying the gene product by using an immobilized ligand corresponding to these.

Figure 11:
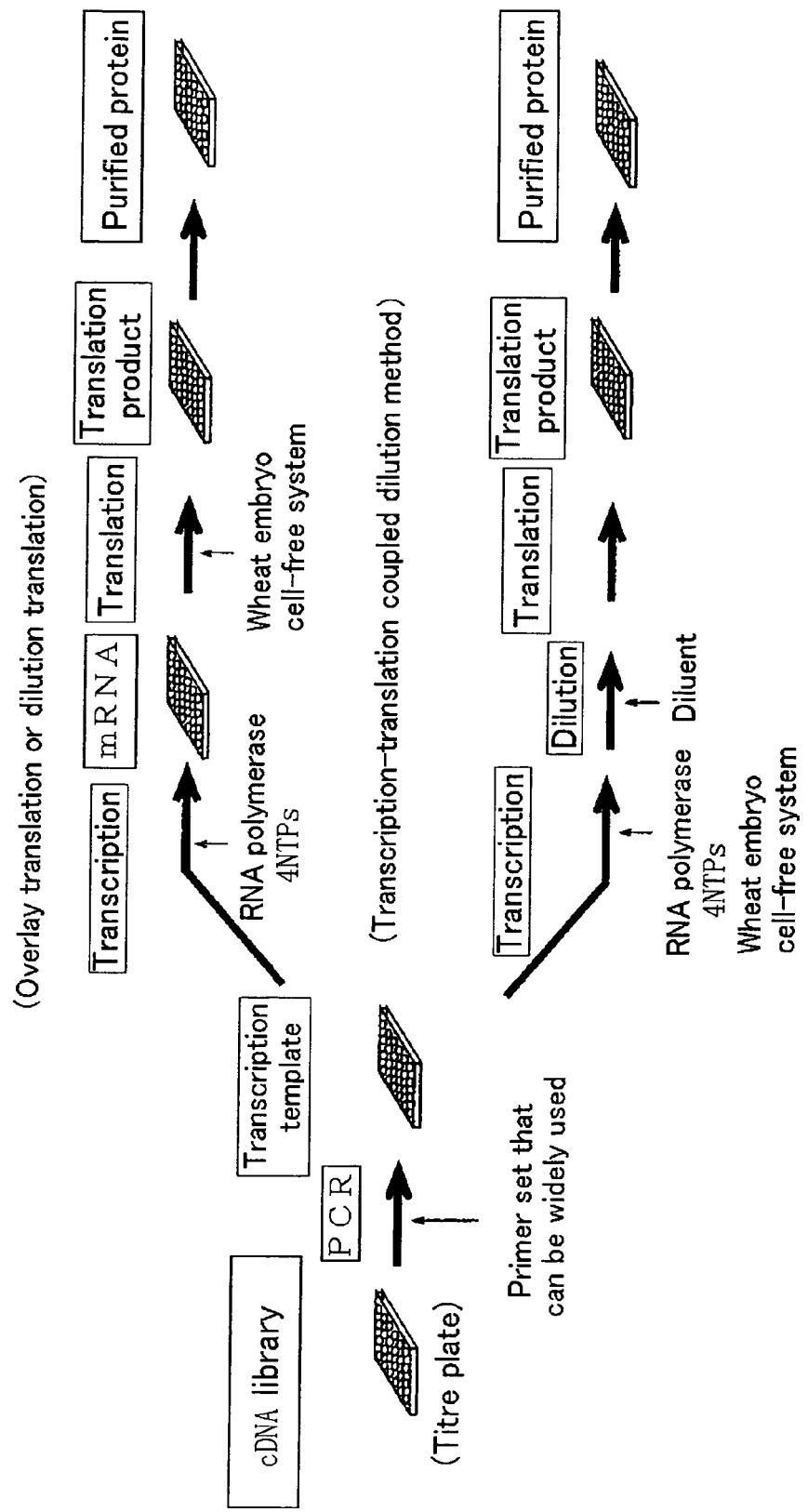
FIG. 11 illustrates the outline of a method for preparing a protein library from a cDNA library.

As FIG. 11 illustrates, for example, a primer set (three 5'-end side ones and one 3'-end side one), according to the present invention, which can be generally used and can be commonly used for all the genes, is used. Using the set permits simply and efficiently synthesizing many proteins at once by the transcription-translation coupled and transcription-translation consecutively diluting cell-free protein synthesis methods.

First of all, cDNAs are added to a reaction vessel. In this embodiment, each cDNA encoding various proteins are added to each well in a commercially available multi-well titer plate such as a 96-well titer plate. Therefore, this permits synthesizing many kinds of proteins at the same time. Thus, a multi-titer plate prepared by adding each of various cDNAs to each well can be used as a cDNA library. A commercially available cDNA can also be used. PCR is carried out by adding the above primer set to the above cDNA library. As a result, a transcription template is formed.

In the case where the transcription-translation coupled dilution protein synthesis method is carried out thereafter, a reaction mixture for the cell-free protein synthesis containing an RNA polymerase, 4NTPs, a wheat embryo extract, and so on (see e.g., Example 5 below) is added to each reaction vessel. Then, the reaction mixture is incubated at about 30° C. to about 45° C., preferably at about 35° C. to about 40° C., to carry out the transcription reaction for a desired time. Subsequently, a diluent is added to the reaction mixture to reduce the concentration of magnesium to a suitable level, and then the translation reaction is carried out at about 20° C. to about 30° C. As a result, a protein is obtained as a translation product.

When the transcription-translation consecutively diluting protein synthesis method is carried out after forming a transcription template, a solution for the transcription containing an RNA polymerase, 4NTPs, and so on (see, e.g., Example 4 below) is added to each reaction vessel, and the resultant mixture is incubated at about 30° C. to about 45° C., preferably at about 35° C. to about 40° C., to carry out the transcription reaction for a desired time. Then, a reaction mixture for the cell-free protein synthesis containing a wheat embryo extract and so on (see, e.g., Example 4) is provided, and the resultant mixture is incubated together at about 20° C. to about 30° C. for the translation reaction.

In addition, as described above, after the transcription is carried out in a solution for the transcription reaction for a desired time, the above reaction mixture for the cell-free protein synthesis can be gently overlayed onto the solution after the transcription reaction in which a translation template was formed, and placed in a reaction vessel (e.g., multi-well titer plate) for the cell-free protein synthesis reaction. In this method, substances contained in solutions in both phases diffuse into the other phase, and both phases are gradually mixed. Therefore, the translation reaction progresses continuously and gradually, and the protein synthesis can be carried out for a long time.

As described above, the present invention has enabled the simple and efficient cell-free protein synthesis using PCR that had been difficult to achieve so far, by the following protein synthesis method:
1) a wheat embryo efficient cell-free protein synthesis system,
2) a method for constructing an mRNA transcription template according to the present invention, and
3) a transcription-translation coupled dilution cell-free protein synthesis method or a transcription-translation consecutively diluting cell-free protein synthesis method.

In addition, using a template DNA for the cell-free protein synthesis, constructed using the conventional single-stranded primer containing the promoter site, the translation amplification structure, and a part of ORF, gave a large amount of low-molecular-weight translation products, i.e., low translation efficiency. The present invention, however, solved this fault. The principle of constructing a transcription template for the cell-free protein synthesis system by the PCR method using the above promoter sequence-divided type primer is not limited to a cell-free protein synthesis system using a wheat embryo extract, but is used as a principle of designing a template in a cell-free protein synthesis system using other cell extracts such as *Escherichia coli*.

If characteristic 5'-end side and 3'-end side primers having sequences complementary to genes inserted into a vector are prepared, using the above primer set that can be commonly used for all genes and can be generally used permits the simple and efficient cell-free protein synthesis from an inserted arbitrary gene. Therefore, the present invention provides the fundamental element technology, for producing genetic products (proteins), that is the base for analyzing the structure and function of numerous genes provided until the completion of the genome project.

EXAMPLES

The present invention is described in detail by citing Examples and Reference Examples below, but the present invention is not limited to the examples below.

Example 1

Designing a Primer for Constructing a Transcription Template and Constructing an mRNA Having a High Translation Template Activity (a Method for Constructing a Transcription Template Paying Attention to the 3'-End Untranslated Sequence Synthesis of an mRNA)

A transcription template was constructed using the PCR method for obtaining an mRNA that is effective for enhancing the translation template activity, has the shortest 3'-end untranslated structure, and has a high translation efficiency.

A template for the PCR was prepared according to conventional methods by integrating a jelly fish GFP gene into pEU (WO01/27260) developed as a plasmid (FIG. 1 a) for the wheat embryo cell-free protein synthesis system illustrated in FIG. 1a. Into this plasmid, the followings are inserted in this order:

1) a promoter sequence of SP6 RNA polymerase upstream of the 5'-end,
2) Ω sequence of tobacco mosaic virus (TMV) that is the translation initiation reaction sequence,
3) GFP gene,
4) the replication origin (Ori) downstream of the 3'-end, and
5) ampicilin resistance gene (Amp$^r$) as a marker gene downstream of 4).

The 5'-end side primer used is a primer containing SP6 primer sequence (5' GCATT TAGGT GACAC TATAG AA 3'-SEQ. ID NO. 6), and the 3'-end side primer is primer I, II, or III (sequence no. 1 in the sequence listing) [FIG. 1a]. These sequences are shown below. These primers were prepared by Amersham-Pharmacia Inc.

Primer I: 5' GGGAA GATAA ACAGT ATTTT 3'-SEQ. ID NO. 7 (for mRNA1 transcription)

Primer II: 5' CCCTC GAGGC GTGGG CCCCA 3'-SEQ. ID NO. 8 (for mRNA2 transcription)

Primer III: 5' AGCGT CAGAC CCCGT AGAAA 3'-SEQ. ID NO. 1 (for mRNA3 transcription)

Using, as a template, the above pEU into which the jelly fish GFP gene was inserted and the above primers, PCR was carried out under the following conditions:
Reaction Mixture for PCR

| 1 x | ExTaq buffer |
|---|---|
| 200 μM | dNTP (deoxyribonucleotide triphosphate) |
| 10 nM | primer (5' GCATT TAGGT GACAC TATAG AA 3') - SEQ. ID NO. 6 |
| 10 nM | primer I, II, or III |
| 0.025 U | ExTaq DNA polymerase |
| 50 pg/μl | template plasmid DNA |

Reaction Condition for PCR
98° C. for 1 min
↓
30 cycles of (98° C. for 10 sec→>60° C. for 30 sec→72° C. for 5 min)
↓
72° C. for 4 min
↓
4° C.

Then, using, as a transcription template, the PCR products obtained as described above, the solution for the transcription prepared as described below using SR6RNA polymerase was incubated at 37° C. for 2 h to give an mRNA as a transcription product.
Solution for Transcription (mRNA Solution)

|  |  | (μl) | final concentration |
|---|---|---|---|
| PCR products |  | 2.5 | 0.4 μl/μl |
| 5 x Buffer |  | 5 | 1 x |
| 25 mM | NTPs | 3 | 3 mM |
| 111 U/μl | RNase inhibitor | 1 | 4.4 U/μl |
| 50 U/μl | SP6 RNA polymerase | 0.75 | 1.5 U/μl |
| Ion-exchanged water (Milli Q) |  | 12.75 |  |
| Sum |  | 25 |  |

The composition of the 5× buffer used here was as follows:

| 5 x buffer |  | Final concentration of 1 x buffer |
|---|---|---|
| 400 mM | HEPES-KOH pH 7.6 | 80 mM |
| 80 mM | Magnesium acetate | 16 mM |
| 10 mM | Spermidine | 2 mM |
| 50 mM | Dithiothreitol | 10 mM |

FIG. 1b illustrates an mRNA molecule having a different base number of the 3'-end untranslated sequence transcribed from a transcription template that was designed/constructed as described above. The mRNA1, mRNA2, and mRNA3 were constructed using primer I, primer II, and primer III (sequence no. 1 in the sequence listing), respectively.

'Cap' in the figure is GFP mRNA having Cap synthesized by adding 7mGppppG to the 5'-end of an mRNA, and was constructed using primer II for mRNA2, so that it has a 3'-end untranslated sequence having 561 bases. 'Circular' in the figure is GFP mRNA constructed using a circular plasmid as a transcription template, and mainly contains two long 3'-end untranslated sequences having 1,900 bases or 5,900 bases. These were prepared according to the method already disclosed in WO01/27260, and were used for the cell-free protein synthesis reaction both as experimental controls.

A translation template activity of the mRNA obtained using the transcription template as described above was examined after the translation reaction for 3 h using a batch wheat embryo cell-free protein synthesis system. The translation reaction was carried out according to the method described in Madin K. et al., (2000) Proc. Natl. Acad. Sci. USA, 97, 559-564 and WO00/68412. In addition, the protein synthesis was assayed using the incorporation of $^{14}$C-leucine as an index, with the expression of the radioactivity count of the Y-axis per unit volume of wheat embryo extract. As a result, as FIG. 1c illustrates, mRNA3 (GFP mRNA having Ω sequence at the 5'-end and an untranslated sequence consisting of 1,896 bases at the 3'-end) transcribed from the template constructed using primer III (sequence no. 1 in the sequence listing) showed a high translation activity. In addition, it became clear that the efficiency is comparable to an mRNA having Cap and an mRNA having a long-chain 3'-end untranslated sequence transcribed from the Circular plasmid.

In other words, it became clear that the method of designing and using, as a primer, a base sequence complementary to a base sequence present between the transcription terminator sequence of ampicilin resistance gene of a vector into which a gene was inserted and Ori, is useful for constructing a DNA base sequence (example, primer III: sequence no. 1 in the sequence listing) that is a transcription template for adding a 3'-end untranslated sequence to the mRNA used for the wheat embryo cell-free protein synthesis system.

Reference Example 1

Designing Primer for Constructing Transcription Template and Constructing Transcription Template by PCR (a Method for Constructing a Transcription Template by the Conventional Method)

Primers for the PCR were constructed for obtaining, by the PCR method, a transcription template for an mRNA having 5'- and 3'-end untranslated structures.

Concerning a 5'-end untranslated structure of an mRNA, adding the following sequence to the mRNA is very effective for enhancing the efficiency of a cell-free protein synthesis reaction:
1) a base sequence derived from alfalfa mosaic virus (AMV),
2) Ω sequence of tobacco mosaic virus (TMV),
3) AMV-Ω sequence obtained by serially linking these, and
4) 29-base Ω sequence obtained by shortening the Ω sequence.
TMV Ω sequence selected from among these 5'-end untranslated structures was used as the
5'-end untranslated sequence, and the 1,896 bases shown in Example 1 above were used as the
3'-end untranslated sequence (see FIG. 1).

Figure 2:
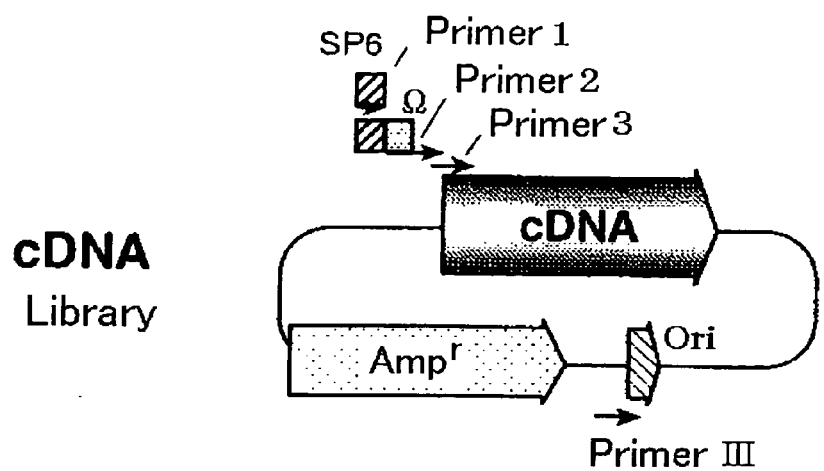
FIG. 2 illustrates a method for constructing a transcription template using 5'-end side primer designed by the conventional method described in Reference Example 1, its transcription product, and its translation activity.
Figure 2:
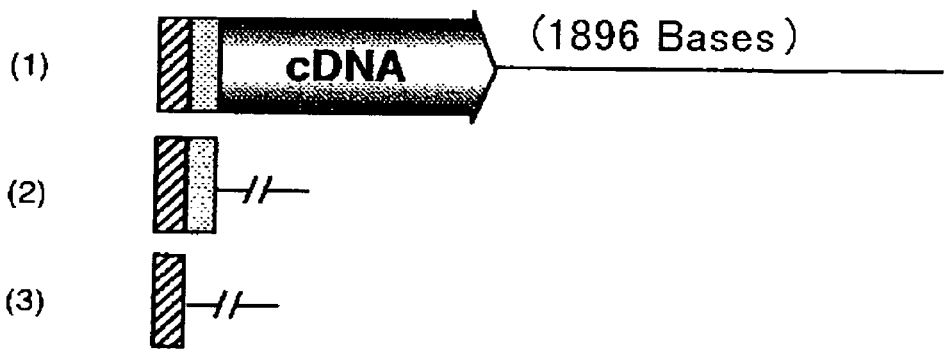
Figure 2:
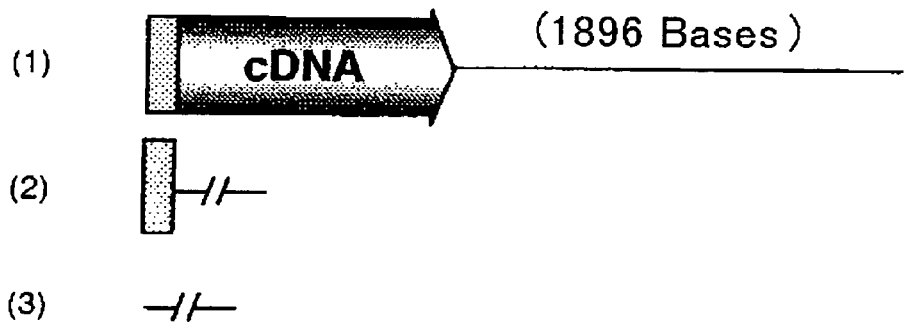

First of all, the conventional PCR method using three primers that are widely used as a method for constructing a 5'-end sequence of a transcription template was investigated (FIG. 2). FIG. 2a illustrates the outline of the PCR method, i.e., the structure of a plasmid into which a gene encoding an objective protein was inserted, three primers (primers 1, 2, and 3) for constructing the 5'-end sequence, and primer III for constructing the 3'-end sequence. Base sequences of primers 1, 2, and 3 are shown hereinafter. 'X' in the base sequence of primer 3 means the 5'-end side base sequence of ORF being inherited to the objective gene. Primer III is identical to the one used in Example 1. These primers were prepared in a manner similar to that of Example 1.
Primer 1: 5' GCATT TAGGT GACAC TATAG AA 3'-SEQ. ID NO. 6
Primer 2: 5' GCATT TAGGT GACAC TATAG AAGTA TTTTT ACAAC AATTA CCAAC AACAA CAACA AACAA CAACA ACATT ACATT TTACA TTCTA CAACT ACAATGXXXX XXXXX XXXXX XXXXX 3'-SEQ. ID NO. 11
Primer 3: 5' ACATT CTACA ACTAC AATGX XXXXX XXXXX XXXXX XXX 3'-SEQ. ID NO. 9

A plasmid prepared by integrating a gene selected from a cDNA library into pUC19 was used as a template for constructing a transcription template. Three cDNAs derived from the rat liver and the GFP gene (molecular weights of translation products from these genes were 25 kDa, 18 kDa, 44 kDa and 27 kDa) were inserted in the plasmid by a manner similar to that of Example 1. PCR was carried out using the above primers in a manner similar to that of Example 1 to produce a transcription template, with which a transcription reaction was experimentally carried out, in a manner similar to that of Example 1, for 2 h to give transcription products.

FIG. 2b illustrates main amplification products obtained by the conventional PCR method and short DNA by-products that were non-specifically formed. FIG. 2c illustrates transcription products synthesized using the amplification products as transcription templates. FIG. 2c (1) illustrates a full-length mRNA capable of giving a full-length translation product. FIG. 2c (2) illustrates an mRNA giving a low-molecular-weight translation product. FIG. 2c (3) illustrates an mRNA having no translation template activity because it lacks the Ω sequence. When considered on biochemical properties in the transcription reaction, a majority of RNA molecules synthesized are supposed to be derived from a PCR product (short DNA).

Figure 3:
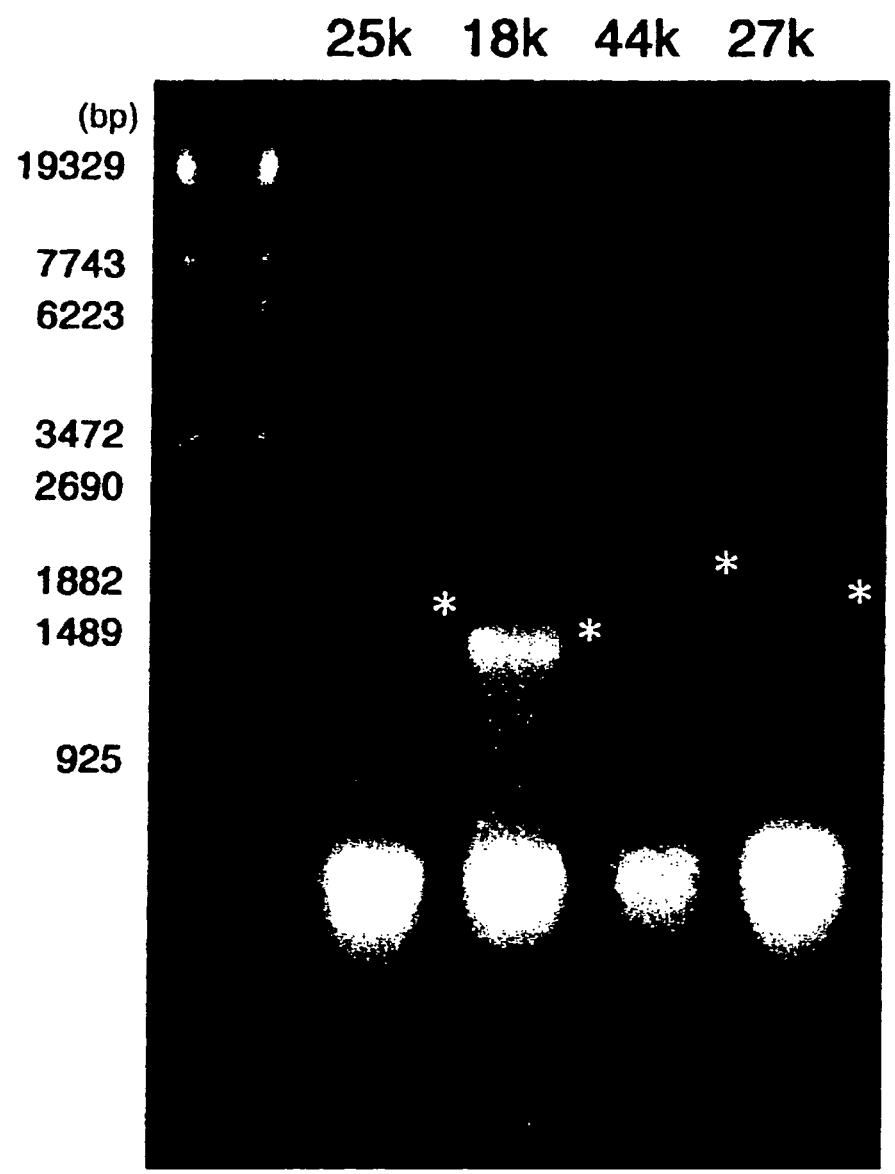
FIG. 3 illustrates an agarose-gel electropherogram of a transcription product obtained from a transcription template constructed using a 5'-end side primer designed by the conventional method described in Reference Example 1. Each lane is an electropherogram of an mRNA obtained using a transcription template prepared from a template plasmid into which one selected from a group consisting of three cDNAs and a GFP gene (molecular weights of translation products are 25 kDa, 18 kDa, 44 kDa, and 27 kDa as shown in the figure) was inserted. The left lane is an electropherogram of molecular-weight markers. The asterisks indicate full-length transcription products.

FIG. 3 illustrates a result of the agarose-gel electrophoresis of the above transcription products by the common procedure, with each lane being a transcription product (i.e., mRNA) prepared from a template plasmid into which one selected from a group consisting of three cDNAs and a GFP gene (molecular weights of translation products are 25 kDa, 18 kDa, 44 kDa, and 27 kDa), with the asterisk being a full-length transcription product. FIG. 3 illustrates that the larger the ORF of the gene is, the lower the transcription efficiency is. In addition, the majority of products transcribed by the method are low-molecular-weight RNA. Therefore, a short DNA molecular species non-specifically formed by the PCR method contain a promoter sequence. This result conformed to the estimation based on the above FIGS. 2b and 2c.

Figure 4:
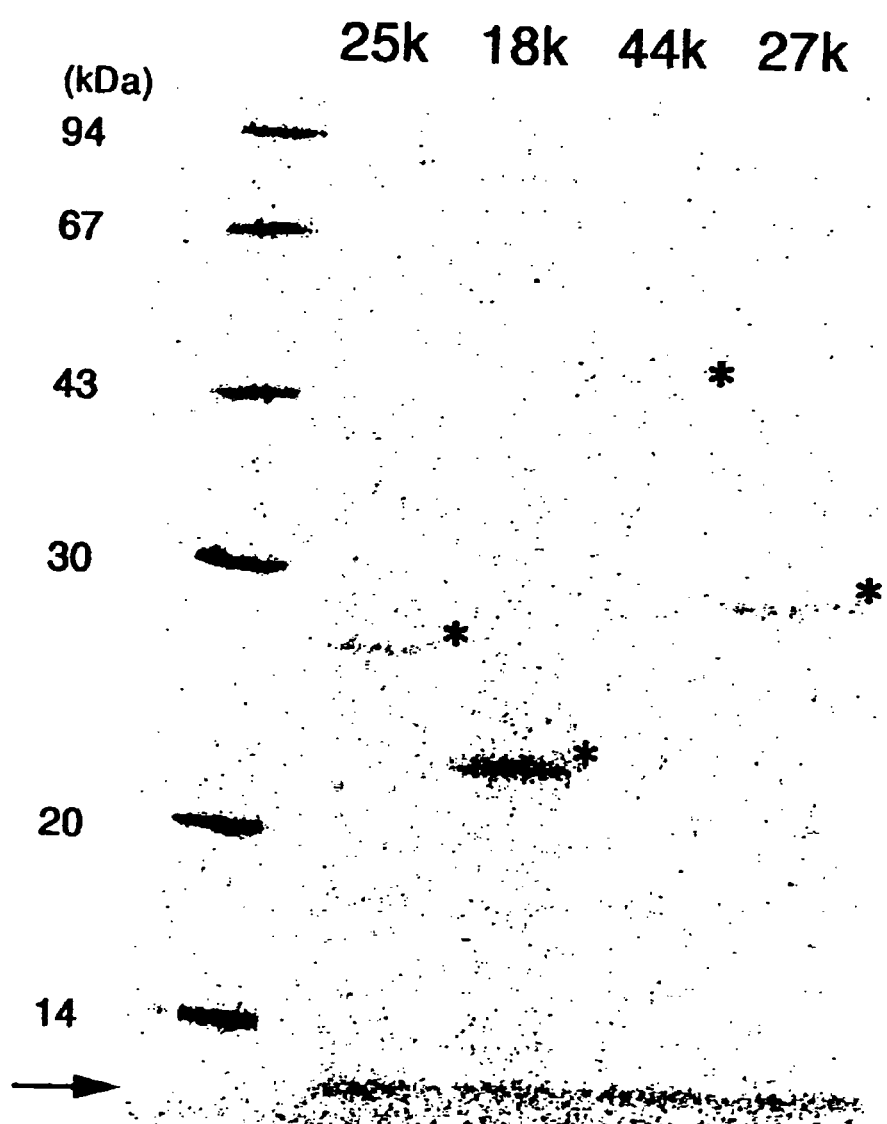
FIG. 4 illustrates an autoradiogram of translation products after the cell-free protein synthesis using a transcription product obtained from a transcription template constructed by the 5'-end side primer designed by the conventional method described in Reference Example 1. Each lane is an electropherogram of a translation product translated from a transcription product obtained by using a transcription template prepared from a template plasmid into which one selected from a group consisting of three cDNAs and a GFP gene (molecular weights of translation products are 25 kDa, 18 kDa, 44 kDa, and 27 kDa as the figure shows) was inserted. The left lane is an electropherogram of molecular weight makers. The asterisks indicate full-length translation products; the arrow indicates a low-molecular-weight product.

Then, without isolating an mRNA having an objective size from each of the above transcription products, each of the transcription products was desalinated. The resultant product was added to a wheat embryo cell-free protein synthesis system. The resultant mixture was incubated for 3 h to give translation products, which were detected by the autoradiography according to a conventional method [Endo, Y. et al., (1992) J. Biotech., 25, 221-230; Madin K. et al., (2000) Proc. Natl. Acad. Sci. USA, 97, 559-564]. The translation reaction was carried out according to the methods described in Madin K. et al., (2000) Proc. Natl. Acad. Sci. USA, 97, 559-564 and WO00/68412. The result is shown in FIG. 4. As shown with asterisks in FIG. 4, small amounts of translation product corresponding to each amount of mRNAs were detected. Among the translation products, the synthesis amount of an 18 kDa protein (see FIG. 3) from a large amount of a transcription product was high. However, a majority of translation products were low-molecular-weight products isolated in a low-molecular-weight region, which is indicated with the arrow in FIG. 4, of an SDS-polyacrylamide gel. This shows that the low-molecular-weight transcription products contain a large amount of mRNAs that keep the Ω sequence that is the 5'-end translation initiation-enhancing structure and a part of the 5'-end side of ORF and lacks the 3'-end side of ORF. These mRNA fragments have a strong affinity to a translation initiation factor, so that they act as strong inhibitors to the synthesis of an objective protein and cause a remarkable reduction of the synthesis yield.

Example 2

Designing Primers for Constructing an Efficient Transcription Template and Constructing an Efficient Transcription Template by the PCR (A method for Constructing a Transcription Template by Paying Attention to the RNA Promoter Sequence of the Transcription Template)

Figure 5:
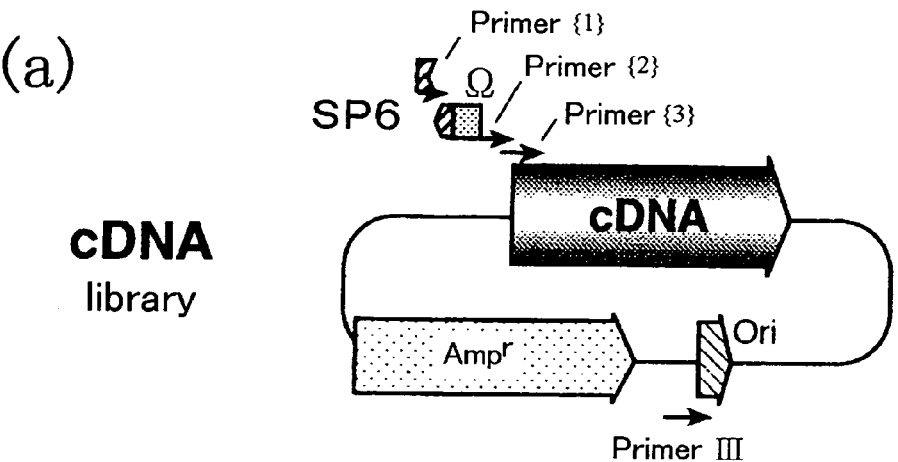
FIG. 5 illustrates a method for constructing a transcription template using the RNA polymerase promoter sequence-divided type primers, its transcription products, and their translation activities in Example 2.
Figure 5:
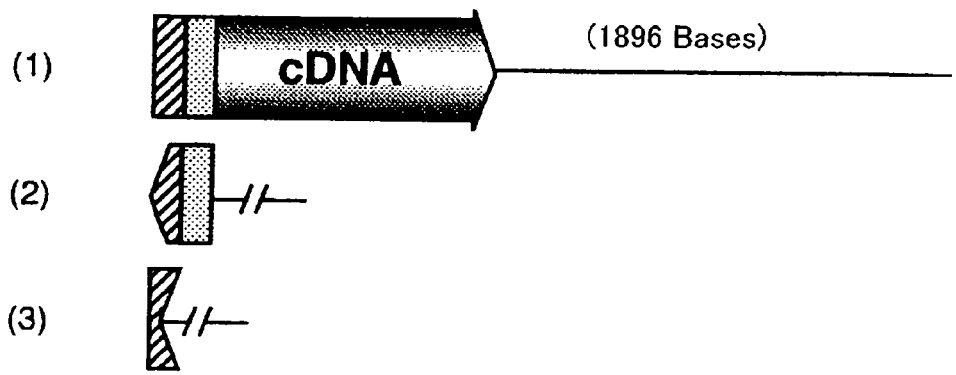
Figure 5:
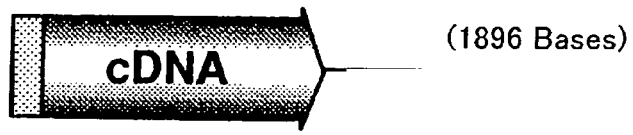

Primers effective for constructing, by the PCR method, an mRNA transcription template having a high translation activity having a 5'-end untranslated sequence that can be used for a cell-free protein synthesis system without isolating an mRNA having an objective size after the transcription reaction are not obtained by the method for designing primers according to the conventional method shown in Reference Example 1. Therefore, based on the principle for adequately utilizing properties of the RNA polymerase, i.e., the fact that the RNA polymerase recognizes promoter structure having a complete base sequence but does not recognize one having an incomplete base sequence, the effective primers were designed and prepared, and a method for constructing a transcription template using the primers, was carried out (FIG. 5).

FIG. 5(a) illustrates the structure of a plasmid into which a gene encoding an objective protein used for the PCR method tested here was inserted, three primers (primers {1}, {2}, and {3}) for constructing the 5'-end sequence, and primer III for constructing the 3'-end sequence. Base sequences of the primers are shown hereinafter. These were prepared in a manner similar to that of Example 1. Primer {1} designed here has a sequence complementary to at least a part of the promoter functional site from the 5'-end of the promoter, but does not have a sequence complementary to at least a part of the 3'-end side RNA polymerase recognition site of the promoter. Primer {2} has a base sequence complementary to at least a part of the 3'-end side RNA polymerase recognition site of the promoter, but does not have a sequence complementary to at least the promoter functional site of the 5'-end side of the promoter. In other words, primers {1} and {2} are promoter sequence-divided type primers. Primer {3} is identical to the above primer 3, and primer III is identical to one used in Example 1. In addition, two steps of PCR were carried out here, so that primer IV (sequence no. 4 in the sequence listing) was synthesized for use as a primer for constructing the 3'-end untranslated sequence. Primer IV was designed by shifting the base sequence of the above primer III (sequence no. 1 in the sequence listing) by three bases, and has a base sequence shown hereinafter. 'X' in the sequences of the following primers means the 5'-end side sequences of ORF being inherited to a gene inserted into the plasmid.

Primer {1}: 5' GCGTA GCATT TAGGT GACAC T 3'-SEQ. ID NO. 2

Primer III: 5' AGCGT CAGAC CCCGT AGAAA 3'-SEQ. ID NO. 1

Primer IV: 5' GTCAG ACCCC GTAGA AAAGA 3'-SEQ. ID NO. 4

Primer {3}: 5' ACATT CTACA ACTAC AATGX XXXXX XXXXX XXXXX XXX 3'-SEQ. ID NO. 9

Primer {2}: 5' GGTGA CACTA TAGAA GTATT TTTAC AACAA TTACC AACAA CAACA ACAAA CAACA ACAAC ATTAC ATTTT ACATT CTACA ACTAC AATG 3'-SEQ. ID NO. 13

Main PCR products amplified using these primers are illustrated in FIG. 5b. It was estimated that substantially no RNA is synthesized from the DNAs shown in FIGS. 5b(2) and 5b(3) because they are seldom recognized by RNA polymerase. In addition, it is expected that a transcription template constructed using a primer thus designed becomes FIG. 5c.

A transcription template was constructed using these primers. First of all, the plasmid that was prepared by integrating a gene selected from a cDNA library into pUC19 and is identical to one used in Reference Example 1 was used as a template for constructing a transcription template. The transcription template was prepared using the above primers by the two-step PCR method under conditions described below. ExTaq DNA polymerase (Takara Bio Inc.) was used as a polymerase for the PCR method.

Mixture for the First-Step PCR (Final Concentration)

| 1 x | ExTaq buffer |
|---|---|
| 200 μM | dNTP (deoxyribonucleoside triphosphate) |
| 10 nM | Primer {3} |
| 10 nM | Primer III |
| 0.025 U | ExTaq DNA polymerase |
| 50 pg/μl | Template plasmid DNA |

Mixture for the Second-Step PCR (Final Concentration)

| 1 x | ExTaq buffer |
|---|---|
| 200 μM | dNTP |
| 100 nM | Primer {1} |
| 100 nM | Primer IV |
| 1 nM | Primer {2} |
| 0.025 U | ExTaq DNA polymerase |
| 0.05 μl | The first PCR products |

PCR Reaction Conditions (The first- and second-step PCRs were carried out under the same conditions)

98° C. for 1 min
↓
30 cycles of (98° C. for 10 sec→60° C. for 30 sec→72° C. for 5 min)
↓
72° C. for 4 min
↓
4° C.

Then, a solution for the transcription, prepared in a manner described below, was incubated using, as a transcription template, PCR products obtained as described above and SP6 RNA polymerase at 37° C. for 2 h to give an mRNA as a transcription product.

Solution for Transcription (mRNA Solution)

|  | (μl) | Final concentration |
|---|---|---|
| PCR products | 10 | 0.4 μl/μl |
| 5 x buffer | 5 | 1 x |
| 25 mM NTPs | 3 | 3 mM |
| 111 U/μl RNase inhibitor | 1 | 4.4 U/μl |
| 50 U/μl SP6 RNA polymerase | 0.75 | 1.5 U/μl |
| Ion-exchanged water (Milli Q) | 5.25 |  |
| Sum | 25 |  |

The composition of 5× buffer used here is identical to one used in Example 1.

Figure 6:
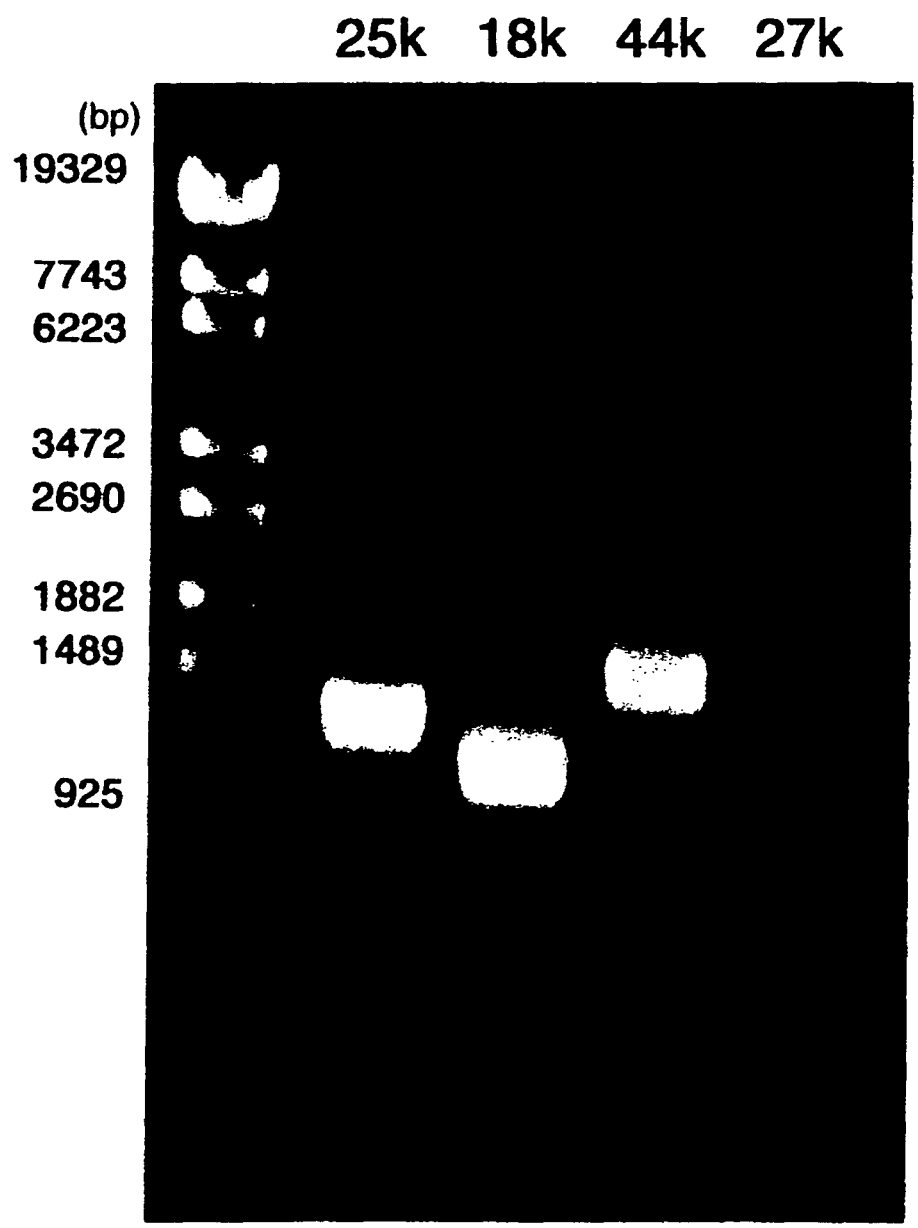
FIG. 6 illustrates an agarose-gel electropherogram of transcription products obtained from a transcription template constructed using the RNA polymerase promoter sequence-divided type primers in Example 2. Each lane is an electropherogram of an mRNA obtained using a transcription template prepared from a template plasmid into which one selected from a group consisting of three cDNAs and a GFP gene (molecular weights of translation products are 25 kDa, 18 kDa, 44 kDa, and 27 kDa as shown in the figure) was inserted. The left lane is an electropherogram of molecular-weight markers.

FIG. 6 illustrates a result of the agarose gel electrophoresis of a transcription product obtained. Any low-molecular-weight transcription product was not detected, but it was confirmed that an RNA having a mobility expected to have as a transcription product from each gene was synthesized.

Figure 7:
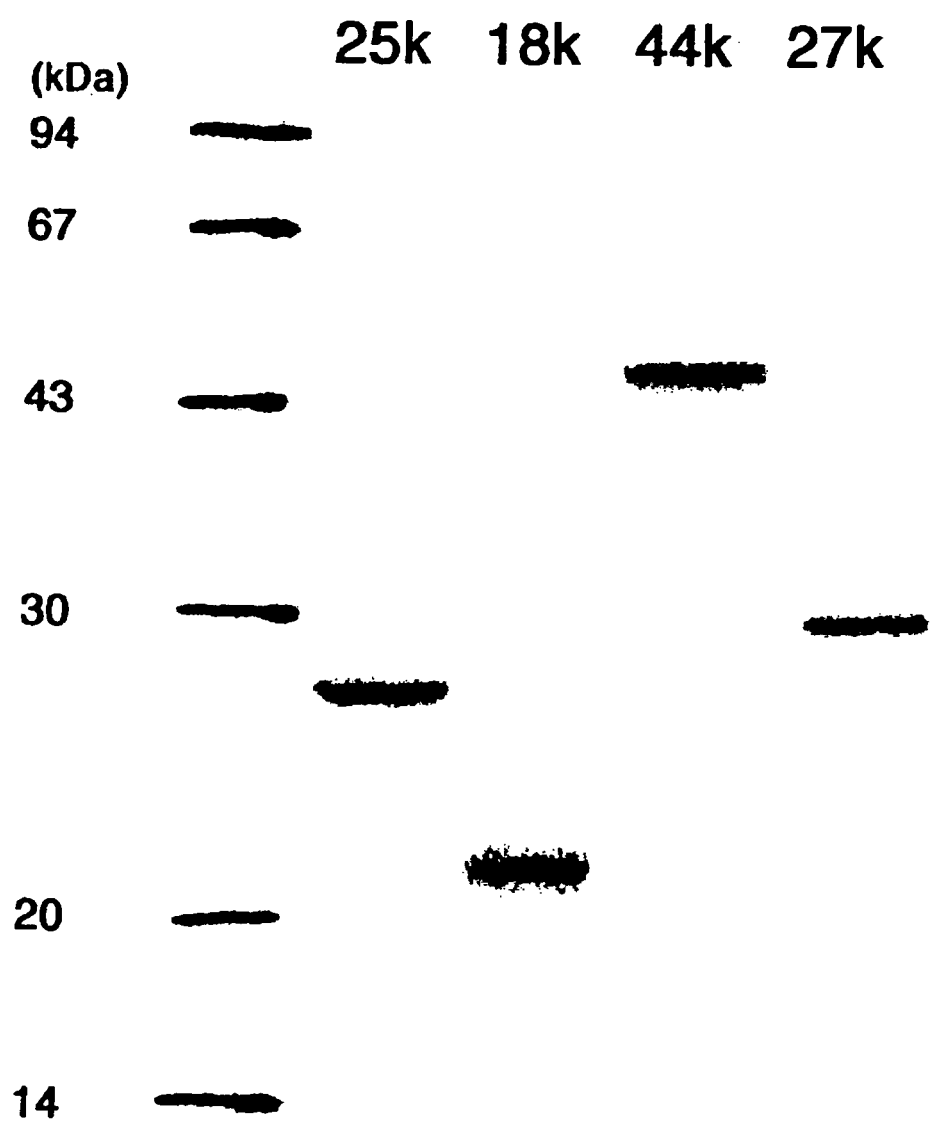
FIG. 7 illustrates an autoradiogram of translation products after the cell-free protein synthesis using a transcription product obtained from a transcription template constructed using the RNA polymerase promoter sequence-divided type primer in Example 2. Each lane shows translation products translated from transcription products obtained using a transcription template prepared from a template plasmid in which one selected from a group consisting of three cDNAs and a GFP gene (molecular weights of translation products are 25 kDa, 18 kDa, 44 kDa, and 27 kDa as shown in the figure) was inserted. The left lane is an electropherogram of molecular-weight markers.

These mRNA specimens were desalinated and were added to a batch wheat embryo cell-free protein synthesis system as a translation template for the protein synthesis. The synthesis reaction was carried out according to methods described in Madin K. et al., (2000) Proc. Natl. Acad. Sci. USA, 97, 559-564 and WO00/68412. FIG. 7 illustrates a result of the autoradiography of products after the protein synthesis reaction at 26° C. for 3 h.

Comparison between FIG. 4 and FIG. 7 shows that the result depends on the transcription template. In case a transcription template designed and constructed by the method according to the present invention was used, any low-molecular-weight translation product was not synthesized, and it was confirmed that any protein is efficiently synthesized.

Figure 8:
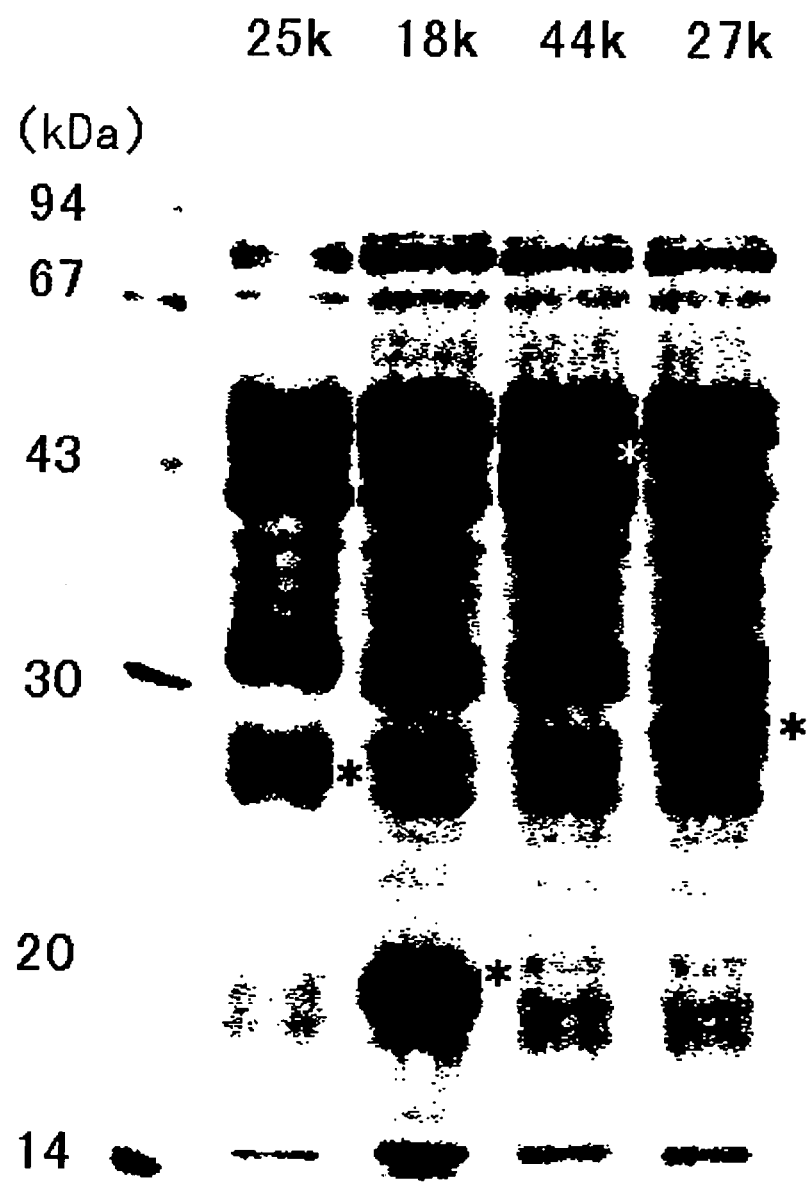
FIG. 8 illustrates the protein synthesis by the dialyzed wheat embryo cell-free protein synthesis method using an mRNA translated from a transcription template constructed using the RNA polymerase promoter sequence-divided type primer in Example 2. Each lane shows products translated from transcription products obtained using a transcription template prepared from a template plasmid in which one selected from a group consisting of three cDNAs and a GFP gene (molecular weights of translation products are 25 kDa, 18 kDa, 44 kDa, and 27 kDa as shown in the figure) was inserted. The left lane is an electropherogram of molecular markers. The asterisks show transcription products.

In addition, the cell-free protein synthesis was carried out using a transcription template obtained by the PCR using primers designed and constructed as described hereinbefore according to the dialysis method using a dialysis membrane described in WO00/68412. One microliter of each reaction mixture was electrophoresed on an SDS gel, and proteins were stained with Coomassie Brilliant Blue. The result is illustrated in FIG. 8. Asterisks in the figure indicate each protein band synthesized from each gene. Patterns of stained bands show that any protein is synthesized at a high yield. Measurements of the stained intensity of bands revealed the following synthesis amounts per 1 ml of the reaction mixture: 25 kDa protein, 0.5 mg; 18 kDa protein, 3.2 mg; 44 kDa protein, 1.2 mg; 27 kDa protein, 1.3 mg.

Example 3

Dilution Wheat Embryo Cell-Free Protein Synthesis Method Using Transcription Template Constructed by PCR Method The continuous cell-free protein synthesis method using a dialysis membrane described in Example 2 was efficient, but the procedure was complicated. Therefore, the conventional batch cell-free protein synthesis reaction was carried out as a simpler method in a reaction mixture for the cell-free protein synthesis containing a low concentration of embryo extract.

A reaction mixture having a composition used for the already known batch cell-free protein synthesis system was used for this method [Madin K. et al., (2000) Proc. Natl. Acad. Sci. USA, 97, 559-564]. First of all, a reaction mixture that contains a wheat embryo extract (concentration, 200 $A_{260nm}$ units/ml) at 48% (v/v) and has the following composition (final concentration) was prepared: 1,000 units/ml ribonuclease inhibitor (RNAsin), 30 mM HEPES-KOH (pH 7.6), 95 mM potassium acetate, 2.65 mM magnesium acetate, 2.85 mM dithiothreitol, 0.5 mg/ml creatine kinase, 1.2 mM ATP, 0.25 mM GTP, 16 mM creatine phosphate, 0.380 mM spermidine, 0.3 mM each of twenty L-type amino acids, and 600 µg/ml mRNA encoding GFP. The mRNA is an mRNA transcribed from a transcription template obtained, by the PCR, by the method identical to one described in Example 2 using promoter sequence-divided type primers described in the above Example 2. In addition, the mRNA has the Ω sequence, but does not have CAP structure at the 5'-end, and has a 3'-end untranslated sequence consisting of 1,896 bases. The above reaction mixture was pre-incubated at 26° C. for 15 min, and was diluted by adding 5 volumes of a diluent containing 30 mM HEPE-KOH (pH 7.6), 95 mM potassium acetate, 2.65 mM magnesium acetate, 2.85 mM dithiothreitol, 1.2 mM ATP, 0.25 mM GTP, 16 mM creatine phosphate, 0.380 mM spermidine, and 0.3 mM each of twenty L-type amino acids, i.e., the dilution method.

Figure 9:
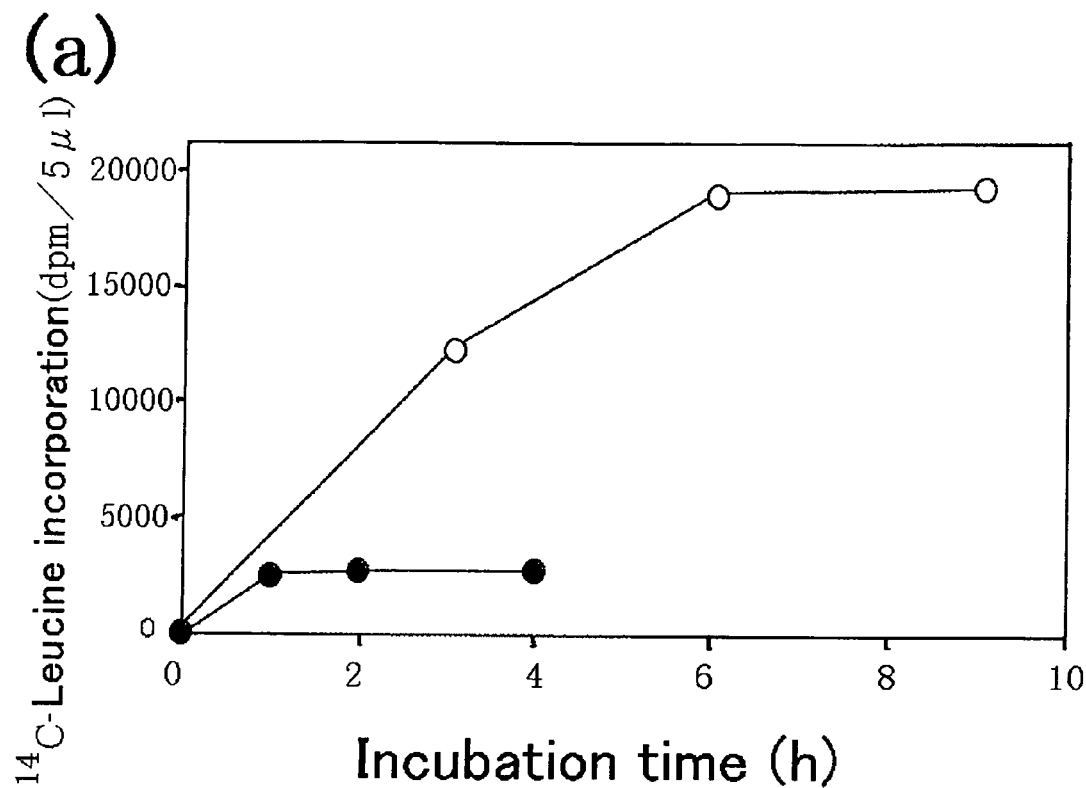
FIG. 9 illustrates the protein synthesis by the dilution wheat embryo cell-free protein synthesis method described in Example 3.
Figure 9:
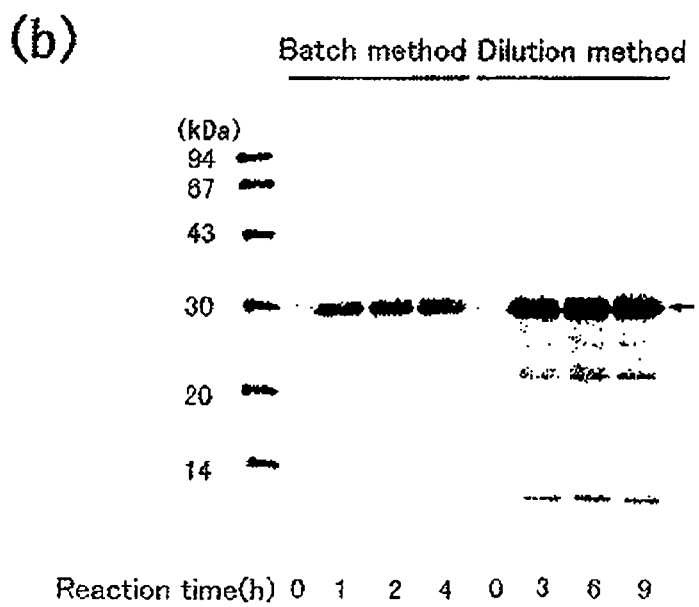

In case the protein synthesis is investigated using the incorporation of an amino acid as an index, 4µ Ci of $^{14}C$-leucine was added to 1 ml of the diluent. After the dilution, the protein synthesis reaction was restarted at 26° C. The result is illustrated in FIG. 9a, with the Y-axis representing the radioactivity count per equal volume of embryo extract. Incorporation of $^{14}C$-leucine into a protein, i.e., protein synthesis reaction, stopped within 1 h by the conventional batch method (●-●), while the synthesis reaction persisted for 9 h by the dilution method (○-○), according to the present invention. The amount of protein synthesized by the dilution method was about 8 times that of the conventional method. An autoradiogram of proteins obtained is shown in FIG. 9b, with the left lane being molecular markers and the arrow being the GFP that is a product of the synthesis. The autoradiogram also revealed that the synthesis reaction continued for 9 h by the dilution method. In addition, the mobility revealed that the synthesis product was synthesized as a full-length protein and was accumulated in the reaction mixture.

The dilution cell-free protein synthesis method shown here does not contain any complex procedure, and permits an efficient cell-free protein synthesis using a transcription template constructed by the PCR.

Example 4

Transcription Using Transcription Template Constructed by PCR and Translation Continuous Dilution Wheat Embryo Cell-Free Protein Synthesis Method Although the dilution wheat embryo cell-free protein synthesis method described in Example 3 gives a high translation efficiency, an mRNA separately transcribed must be added to the cell-free protein synthesis system, i.e., the procedure is complex. Then, a new transcription-translation consecutively diluting cell-free protein synthesis method was carried out. The new method is a combination of the conventional transcription system, the translation system, and the dilution method.

First of all, a solution for transcription was prepared as described below, wherein the PCR product is a transcription template constructed by a method similar to that of Example 2 using the promoter sequence-divided type primer described in the above Example 2, and the 3'-end side primer complementary to sequence is present between $Amp^r$ and Ori. The solution for transcription was incubated at 37° C. for 3 h to synthesize an mRNA.

Solution for Transcription (mRNA Solution)

|  | (µl) | Final concentration |
|---|---|---|
| PCR product | 10 | 0.4 µl/µl |
| 5 x Buffer | 5 | 1 x |
| 25 mM NTPs | 3 | 3 mM |
| 111 U/µl RNase inhibitor | 1 | 4.4 U/µl |
| 50 U/µl SP6 RNA polymerase | 0.75 | 1.5 U/µl |
| Ion-exchanged water (Milli Q) | 5.25 |  |
| Sum | 25 |  |

Only the final concentration of NTPs of the above solution for the transcription was changed to 2.5 mM or 1.5 mM, and the transcription reaction was carried out with each condition, with the composition of 5× buffer used here being identical to that of Example 1.

The mRNA solution obtained contains higher concentrations of magnesium ion, ATP, and GTP than the optimal concentrations for the translation reaction. Therefore, it is not enough for serially carrying out the translation reaction in the same vessel to only add a wheat embryo extract for the cell-free protein synthesis. Therefore, the following reaction mixture for the cell-free protein synthesis was added to 25 µl of the mRNA solution obtained. Thus, the concentration of magnesium ion is diluted to the optimal one for the translation reaction, i.e., 3.19 mM, and the dilution permits the synthesis of proteins.

Reaction Mixture

|  |  | (µl) | Final concentration |
|---|---|---|---|
| Wheat embryo extract |  | 12 | 8% |
| 1,000 mM | HEPES-KOH pH 7.8 | 2 | 30 mM |
| 4,000 mM | Potassium acetate | 3.5 | 100 mM |
| 1,000 mM | Magnesium acetate | 0 | 3.19 mM |
| 10 mM | Spermidine | 1 | 0.4 mM |
| 50 mM | Dithiothreitol | 1.5 | 2.5 mM |
| 2.5 mM | Amino acid mixture | 16.6 | 0.3 mM |
| 100 mM | ATP | 1.3 | 1.2 mM |
| 20 mM | GTP | 0 | 0.33 mM |
| 500 mM | Creatine phosphate | 4.8 | 16 mM |
| 111 U/µl | RNase inhibitor | 0 | 0.74 U/µl |
| 15 µg/µl | tRNA | 2 | 0.2 µg/µl |
| 40 µg/µl | Creatine kinase | 1.5 | 0.4 µg/µl |
| 100 µCi/ml | $^{14}$C-Leucine | 3 | 4 µCi/ml |
| Ion-exchanged water (MillQ) |  | 75.8 |  |

This dilution procedure reduced the concentrations of ribonucleoside triphosphate that remains as transcription substrate (inhibitor in translation reaction) and pyrophosphate by-product to one sixth. After this dilution procedure, the reaction mixture was re-incubated at 26° C. (optimum temperature for translation). The result is shown in FIG. 10.

FIG. 10a illustrates the synthesis of GFP as measured as the incorporation of an amino acid, showing that the synthesis reaction continued for 9 h in case solutions for transcription containing NTPs at 2.5 mM (□-□, middle size) or 3.5 mM (□-□, large size) and that the amount of protein synthesized was about 8 times that of the batch method (●-●). This synthesis efficiency is at a level comparable to that of the mRNA-added dilution cell-free protein synthesis system (○-○) described in Example 3.

Figure 10:
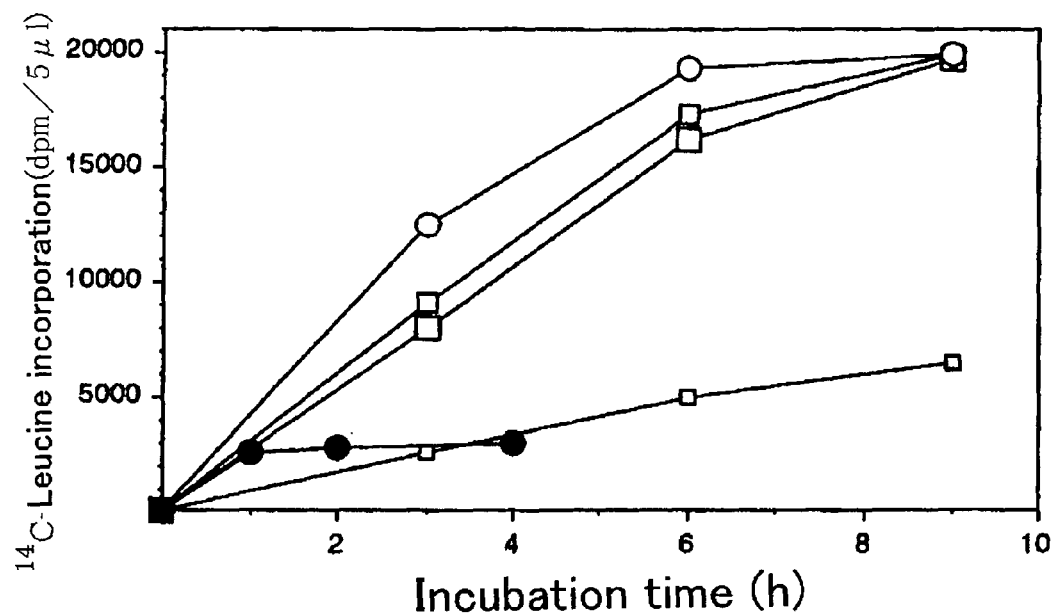
FIG. 10 illustrates the protein synthesis by the transcription-translation coupled dilution wheat embryo cell-free protein synthesis method in Example 4.
Figure 10:
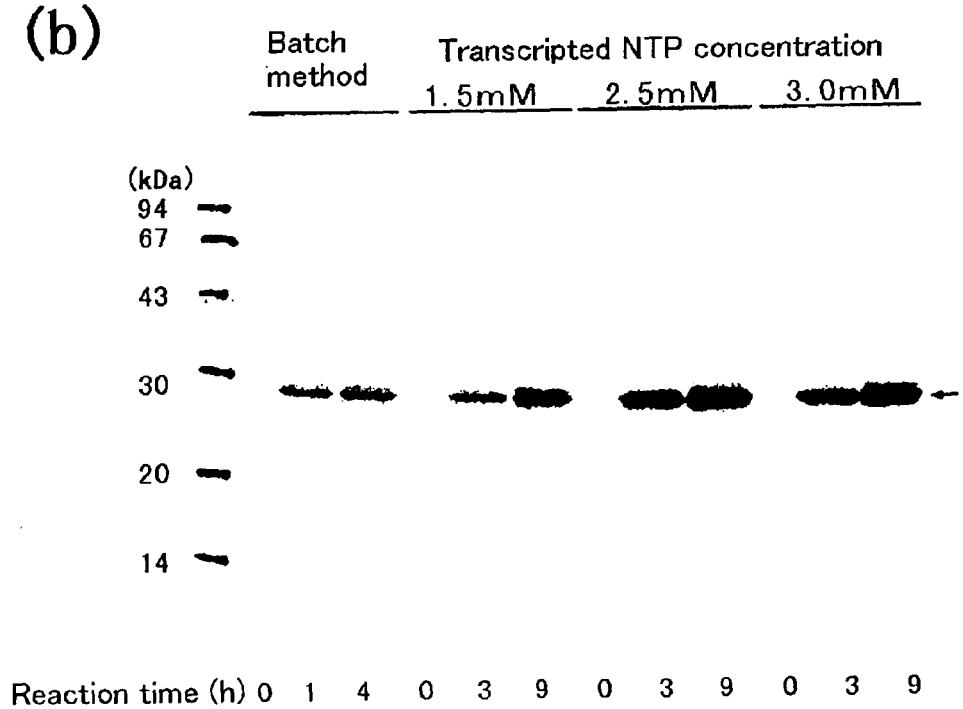

FIG. 10 b illustrates an autoradiogram of the protein obtained. The figure shows that the transcription-translation consecutively diluting method permits carrying out the synthesis reaction for 9 h, that the synthesis product is formed as a full-length protein as judged from its mobility, and that the protein is accumulated in the reaction mixture. The amount of the protein synthesized was maximal in case the ribonucleotide was added at 2.5 mM (□-□, middle size) for the transcription reaction. After the SDS-gel electrophoresis, the protein was stained with Coomassie Brilliant Blue to measure the strength of the stained band of GFP, showing that 0.82 mg of GFP was synthesized per 1 ml of the reaction mixture.

Using a transcription template constructed using a promoter sequence-divided type primer and a 3'-end side primer homologous to the sequence present between Amp$^r$ and Ori in a manner similar to Example 2, permitted carrying out the transcription-translation consecutively diluting wheat embryo cell-free protein synthesis method to efficiently and simply synthesize a protein.

Example 5

Transcription-Translation Coupled Diluting Wheat Embryo Cell-Free Protein Synthesis Method Using a Transcription Template Constructed by the PCR Method First of all, a reaction mixture was prepared so as to contain (final concentration) a wheat embryo extract (concentration of 200 A$_{260nm}$ units/ml) at 48% (v/v), 1,000 units/ml ribonuclease inhibitor (RNAsin), 30 mM HEPES-KOH (pH 7.6), 95 mM potassium acetate, 16 mM magnesium acetate, 2.85 mM dithiothreitol, 0.5 mg/ml creatine kinase, 2.5 mM ATP, 2.5 mM. GTP, 2.5 mM UTP, 2.5 mM CTP, 1,500 units/ml SP6 RNA polymerase, 16 mM creatine phosphate, 1.48 mM spermidine, 0.3 mM each of twenty L-type amino acids, and 25 µg/ml DNA that is a transcription template constructed using a promoter sequence-divided type primer described in Example 2 and a 3'-end side primer complementary to the sequence present between Amp$^r$ and Ori by the method described in Example 2. A gene into which GFP was inserted was used. The above reaction mixture was incubated at 30° C. for 3 h to transcript the mRNA.

Concentrations of magnesium ion, ATP, and GTP in this synthesis reaction mixture are remarkably high compared with optimal concentrations for translation, so that normal protein synthesis does not progress although transcription progresses. In order to initiate the protein synthesis reaction, the concentration of magnesium ions was reduced to the optimal level (3.19 mM) by adding, to the reaction mixture, five volumes of a diluent containing 30 mM HEPES-KOH (pH 7.6), 95 mM potassium acetate, 0.4 mM magnesium acetate, 2.85 mM dithiothreitol, 0.94 mM ATP, 0.25 mM GTP, 16 mM creatine phosphate, 0.380 mM spermidine, and 0.3 mM each of twenty L-type amino acids and, in case protein synthesis is assayed as measured by the incorporation of an amino acid, 4 µCi of $^{14}$C-leucine. Protein synthesis comparable to that of Example 4 was confirmed by this method.

The transcription-translation coupled or transcription-translation consecutively diluting cell-free protein synthesis method does not contain any complex procedures, is simple, and permitted efficiently synthesizing a protein using a cell-free system and a transcription template constructed by the PCR method.

INDUSTRIAL APPLICABILITY

The present invention permitted designing and constructing a transcription template, for cell-free protein synthesis, that can be widely used, has a high transcription template activity, and can be simply constructed, and constructed a simple cell-free protein synthesis method using the transcription template. In other words, techniques for 1) designing an mRNA keeping a high translation template activity, 2) designing a primer for constructing, from a gene, a transcription template that can be widely used and permits suppressing the transcription background and so on for transcribing an mRNA having a high translation efficiency based on the PCR technique, and 3) simply synthesizing a protein using a constructed transcription template for the cell-free protein synthesis, were established.

According to the present invention, for a gene that was inserted into any vector, preparing two characteristic 5' end side and 3'-end side primers having sequences complementary to the gene and using primers that can be commonly used for all genes (three 5'-end side primers and one 3'-end side primer) permit the simple and efficient cell-free protein synthesis. Also, as described above, the present invention is advantageous over the conventional consecutive cell-free protein synthesis method that requires complex apparatuses and procedures. Therefore, the present invention would provide the fundamental element technology, for producing gene products (proteins), which is a base for functionally and structurally analyzing numerous genes that are to be provided until the completion of the genome project. The present invention is important as the elemental technology for automating the cell-free protein synthesis system, in particular, developing the high-throughput fully-automated cell-free protein synthesis robot. Therefore, the present invention will make a great contribution to a large area, including the basic biology such as the structural biology and the biochemistry and the development and production of medicines as its application.

SEQUENCE LISTING FREE TEXT

Sequence no. 1 in the sequence listing: a polynucleotide designed to construct primers for the PCR.
Sequence no. 2 in the sequence listing: a polynucleotide designed to construct primers for the PCR.
Sequence no. 3 in the sequence listing: a polynucleotide designed to construct primers for the PCR.
Sequence no. 4 in the sequence listing: a polynucleotide designed to construct primers for the PCR.
Sequence no. 5 in the sequence listing: a polynucleotide designed based on tobacco mosaic virus Ω sequence to construct primers for the PCR.
Sequence no. 6 in the sequence listing: a polynucleotide designed to construct primers for the PCR.
Sequence no. 7 in the sequence listing: a polynucleotide designed to construct primers for the PCR.
Sequence no. 8 in the sequence listing: a polynucleotide designed to construct primers for the PCR.
Sequence no. 9 in the sequence listing: a polynucleotide designed to construct primers for the PCR.
Sequence no. 10 in the sequence listing: a polynucleotide designed to construct primers for the PCR.
Sequence no. 11 in the sequence listing: a polynucleotide designed to construct primers for the PCR.
Sequence no. 13 in the sequence listing: a polynucleotide designed to construct primers for the PCR.

What is claimed is:

1. A method comprising:
    constructing, by PCR, a transcription template having a promoter base sequence for cell-free protein synthesis using two polynucleotides (A) and (B) having base sequences complementary to different parts of the promoter base sequence, wherein
    (i) polynucleotide (A) is a 5'-end side primer that has a base sequence complementary to a part of a base sequence at the 5'-end of the promoter base sequence and
    (ii) polynucleotide (B) is a 5'-end side primer that has a base sequence different from the base sequence of polynucleotide (A) and is complementary to a part of a base sequence at the 3'-end of the promoter base sequence; and
    (iii) a part of a base sequence at the 3'-end of polynucleotide (A) overlaps a part of a base sequence at the 5'-end of polynucleotide (B);
    wherein both polynucleotides (A) and (B) are used together to construct the transcription template and transcription only occurs when polynucleotides (A) and (B) are used together.

2. The method of claim 1, wherein polynucleotide (B) comprises a GA or GAA sequence, a base sequence providing the translational amplification of an mRNA, the translation initiation codon ATG, and/or a base sequence complementary to a part of an open reading frame or a sequence upstream of the open reading frame of a gene of interest, in this order.

3. The method of claim 2, wherein polynucleotide (A) comprises a histidine tag or a glutathione S-transferase, and polynucleotide (B) comprises a base sequence for synthesizing a tag that is inserted between the initiation codon and the open reading frame.

4. A method comprising:
    constructing by PCR, a transcription template having a promoter base sequence for cell-free protein synthesis using three 5'-end side primers, wherein
    (i) at least one of the following is used as a 5'-end side primer of the transcription template,
        a) a polynucleotide having a base sequence shown by SEQ ID NO:2,
        b) a polynucleotide having a base sequence obtained by linking the omega sequence derived from a tobacco mosaic virus and the translation initiation codon ATG, to a base sequence shown by SEQ ID NO:3, and
        c) a polynucleotide having a base sequence obtained by linking the translation initiation codon ATG and a 5'-end side base sequence of an open reading frame of a gene to be transcribed, in this order, to a base sequence shown by SEQ ID NO:5, and
    (ii) a polynucleotide having a base sequence shown by SEQ ID NO:1 is used as a 3'-end side primer of the transcription template.

* * * * *